(12) United States Patent
Hiddessen et al.

(10) Patent No.: US 9,764,322 B2
(45) Date of Patent: Sep. 19, 2017

(54) SYSTEM FOR GENERATING DROPLETS WITH PRESSURE MONITORING

(71) Applicant: Bio-Rad Laboratories, Inc., Hercules, CA (US)

(72) Inventors: Amy L. Hiddessen, Tracy, CA (US); Kevin D. Ness, Pleasanton, CA (US); Benjamin J. Hindson, Livermore, CA (US); Donald A. Masquelier, Tracy, CA (US); Erin R. Chia, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/351,354

(22) Filed: Nov. 14, 2016

(65) Prior Publication Data

US 2017/0151558 A1    Jun. 1, 2017

Related U.S. Application Data

(60) Continuation-in-part of application No. 12/954,634, filed on Nov. 25, 2010, and a continuation-in-part of
(Continued)

(51) Int. Cl.
*B01L 3/00* (2006.01)
*B01F 3/00* (2006.01)
(Continued)

(52) U.S. Cl.
CPC .......... *B01L 3/50273* (2013.01); *B01L 3/502* (2013.01); *B01L 3/502784* (2013.01); *B01L 3/52* (2013.01);
(Continued)

(58) Field of Classification Search
CPC ................ C12Q 1/686; B01L 2200/14; B01L 2300/0829; B01L 2400/049;
(Continued)

(56) References Cited

U.S. PATENT DOCUMENTS

| 3,575,220 A | 4/1971 | Davis et al. |
| 4,051,025 A | 9/1977 | Ito |

(Continued)

FOREIGN PATENT DOCUMENTS

| CN | 101227972 A | 7/2008 |
| EP | 1522582 A2 | 4/2005 |

(Continued)

OTHER PUBLICATIONS

3M Specialty Materials, "3M Fluorinert Electronic Liquid FC-3283," product information guide, issued Aug. 2001.
(Continued)

*Primary Examiner* — Jennifer Wecker
(74) *Attorney, Agent, or Firm* — Kolisch Hartwell, P.C.

(57) ABSTRACT

System, including methods, apparatus, and kits, for forming emulsions. In an exemplary method of generating droplets, a device may be selected that includes a plurality of emulsion-formation units each including a sample well, a continuous-phase well, a droplet well, and a channel network that fluidically interconnects the wells and creates a droplet-generation region. A discrete volume of sample-containing fluid may be placed into the sample well of each emulsion-formation unit, and a discrete volume of continuous-phase fluid into the continuous-phase well of each emulsion-formation unit. Pressure may be applied to the device with a fluidics assembly after the step of placing, such that the plurality of emulsion-formation units generate droplets in parallel with one another. A pressure signal may be detected from the fluidics assembly. Application of the pressure may
(Continued)

be stopped when the pressure signal indicates that a sample well is empty.

16 Claims, 12 Drawing Sheets

Related U.S. Application Data application No. 13/400,030, filed on Feb. 17, 2012, now abandoned, and a continuation-in-part of application No. 14/020,742, filed on Sep. 6, 2013, and a continuation-in-part of application No. 14/159,410, filed on Jan. 20, 2014, now Pat. No. 9,492,797, and a continuation-in-part of application No. 14/201,752, filed on Mar. 7, 2014, and a continuation-in-part of application No. 14/848,311, filed on Sep. 8, 2015, and application No. 14/159,410, which is a continuation-in-part of application No. 12/586,626, filed on Sep. 23, 2009, now Pat. No. 9,156,010, and a continuation-in-part of application No. 12/862,542, filed on Aug. 24, 2010, now Pat. No. 9,194,861, and a continuation-in-part of application No. 12/890,550, filed on Sep. 24, 2010, now Pat. No. 8,633,015, and a continuation-in-part of application No. 13/245,575, filed on Sep. 26, 2011, now abandoned, and a continuation-in-part of application No. 13/945,661, filed on Jul. 18, 2013, now Pat. No. 9,417,190, and a continuation-in-part of application No. 12/962,507, filed on Dec. 7, 2010, now Pat. No. 9,216,392, and a continuation-in-part of application No. 12/962,511, filed on Dec. 7, 2010, now Pat. No. 9,623,384, and a continuation-in-part of application No. 12/962,502, filed on Dec. 7, 2010, now Pat. No. 9,248,417, and a continuation-in-part of application No. 12/963,523, filed on Dec. 8, 2010, now Pat. No. 9,126,160, and a continuation-in-part of application No. 13/039,233, filed on Mar. 2, 2011, now Pat. No. 8,709,762, and a continuation-in-part of application No. 12/976,827, filed on Dec. 22, 2010, now Pat. No. 9,598,725, and a continuation-in-part of application No. 13/341,669, filed on Dec. 30, 2011, now Pat. No. 9,500,664, and a continuation-in-part of application No. 13/341,678, filed on Dec. 30, 2011, now Pat. No. 8,730,479, and a continuation-in-part of application No. 13/072,673, filed on Mar. 25, 2011, now Pat. No. 9,132,394, and a continuation-in-part of application No. 13/341,688, filed on Dec. 30, 2011, now Pat. No. 9,393,560, and a continuation-in-part of application No. 13/287,120, filed on Nov. 1, 2011, now Pat. No. 9,089,844, and a continuation-in-part of application No. 13/424,304, filed on Mar. 19, 2012, now Pat. No. 9,222,128, and a continuation-in-part of application No. 13/548,062, filed on Jul. 12, 2012, now Pat. No. 8,951,939, and a continuation-in-part of application No. PCT/US2012/048198, filed on Jul. 25, 2012, and a continuation-in-part of application No. 13/562,198, filed on Jul. 30, 2012, now Pat. No. 8,663,920, and a continuation-in-part of application No. 13/287,095, filed on Nov. 1, 2011, now abandoned, and a continuation-in-part of application No. 13/863,231, filed on Apr. 15, 2013, now Pat. No. 9,399,215, and application No. 12/890,550, which is a continuation-in-part of application No. 12/586,626, filed on Sep. 23, 2009, now Pat. No. 9,156,010, and application No. 13/245,575, which is a continuation of application No. 12/586,626, filed on Sep. 23, 2009, now Pat. No. 9,156,010, and application No. 13/945,661, which is a continuation-in-part of application No. 13/251,016, filed on Sep. 30, 2011, now abandoned, and a continuation-in-part of application No. 13/245,575, filed on Sep. 26, 2011, now abandoned, and a continuation-in-part of application No. 12/976,827, filed on Dec. 22, 2010, now Pat. No. 9,598,725, and application No. 12/962,507, which is a continuation of application No. 12/586,626, filed on Sep. 23, 2009, now Pat. No. 9,156,010, and application No. 12/962,511, which is a continuation of application No. 12/586,626, filed on Sep. 23, 2009, now Pat. No. 9,156,010, and application No. 12/962,502, which is a continuation of application No. 12/586,626, filed on Sep. 23, 2009, now Pat. No. 9,156,010, and application No. 12/963,523, which is a continuation of application No. 12/586,626, filed on Sep. 23, 2009, now Pat. No. 9,156,010, and application No. 13/341,669, which is a continuation of application No. PCT/US2011/030101, filed on Mar. 25, 2011, and application No. 13/341,678, which is a continuation of application No. PCT/US2011/030077, filed on Mar. 25, 2010, and application No. 13/072,673, which is a continuation-in-part of application No. 12/586,626, filed on Sep. 23, 2009, now Pat. No. 9,156,010, and application No. 13/341,688, which is a continuation of application No. PCT/US2011/030097, filed on Mar. 25, 2011, and application No. 13/287,095, which is a continuation-in-part of application No. 12/976,827, filed on Dec. 22, 2010, now Pat. No. 9,598,725, and application No. 14/848,311, which is a division of application No. 13/385,277, filed on Feb. 9, 2012, now Pat. No. 9,127,312.

(60) Provisional application No. 61/194,043, filed on Sep. 23, 2008, provisional application No. 61/206,975, filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009, provisional application No. 61/275,860, filed on Sep. 2, 2009, provisional application No. 61/309,837, filed on Mar. 2, 2010, provisional application No. 61/309,845, filed on Mar. 2, 2010, provisional application No. 61/341,218, filed on Mar. 25, 2010, provisional application No. 61/317,635, filed on Mar. 25, 2010, provisional application No. 61/380,981, filed on Sep. 8, 2010, provisional application No. 61/409,106, filed on Nov. 1, 2010, provisional application No. 61/409,473, filed on Nov. 2, 2010, provisional application No. 61/410,769, filed on Nov. 5, 2010, provisional application No. 61/417,241, filed on Nov. 25, 2010, provisional application No. 61/341,218, filed on Mar. 25, 2010, provisional application No. 61/317,684, filed on Mar. 25, 2010, provisional application No. 61/317,635, filed on Mar. 25, 2010, provisional application No. 61/467,347, filed on Mar. 24, 2011, provisional application No. 61/341,065, filed on Mar. 25, 2010, provisional application No. 61/467,347, filed on Mar. 24, 2011, provisional application No. 61/409,106, filed on Nov. 1, 2010, provisional application No. 61/409,473, filed on Nov. 2, 2010, provisional application No. 61/410,769, filed on Nov. 5, 2010, provisional application No. 61/454,373, filed on Mar. 18, 2011, provisional application No. 61/507,082, filed on Jul. 12, 2011, provisional application No. 61/510,013, filed on Jul. 20, 2011, provisional application No. 61/511,445, filed on Jul. 25, 2011, provisional application No. 61/513,474, filed on Jul. 29, 2011, provisional application No. 61/601,514, filed on Feb. 21, 2012, provisional application No. 61/624,199, filed on Apr. 13, 2012, provisional application No. 61/264,591, filed on Nov. 25, 2009, provisional application No. 61/309,845, filed on Mar. 2, 2010, provisional application No. 61/309,837, filed on Mar. 2, 2010, provisional application No. 61/317,684, filed on Mar. 25, 2010, provisional application No. 61/317,635, filed on Mar. 25, 2010, provisional application No. 61/317,639, filed on Mar. 25, 2010, provisional application No. 61/341,065, filed on Mar. 25, 2010, provisional application No. 61/341,218, filed on Mar. 25, 2010, provisional application No. 61/380,981, filed on Sep. 8, 2010, provisional application No. 61/409,106, filed on Nov. 1, 2010, provisional application No. 61/409,473, filed on Nov. 2, 2010, provisional application No. 61/410,769, filed on Nov. 5, 2010, provisional application No. 61/444,674, filed on Feb. 18, 2011, provisional application No. 61/449,580, filed on Mar. 4, 2011, provisional application No. 61/453,537, filed on Mar. 16, 2011, provisional application No. 61/478,777, filed on Apr. 25, 2011, provisional application No. 61/488,667, filed on May 20, 2011, provisional application No. 61/490,040, filed on May 25, 2011, provisional application No. 61/697,982, filed on Sep. 7, 2012, provisional application No. 61/775,415, filed on Mar. 8, 2013, provisional application No. 61/441,209, filed on Feb. 9, 2011, provisional application No. 61/444,539, filed on Feb. 18, 2011, provisional application No. 61/454,373, filed on Mar. 18, 2011, provisional application No. 61/476,115, filed on Apr. 15, 2011, provisional application No. 61/478,777, filed on Apr. 25, 2011, provisional application No. 61/484,197, filed on May 9, 2011, provisional application No. 61/490,055, filed on May 25, 2011.

(51) Int. Cl.
  *B01F 3/08* (2006.01)
  *B01L 9/00* (2006.01)
  *C12Q 1/68* (2006.01)
  *G01N 35/08* (2006.01)
  *B01F 13/00* (2006.01)
  *B01F 5/00* (2006.01)
  *B01F 5/02* (2006.01)

(52) U.S. Cl.
  CPC .............. *B01L 9/527* (2013.01); *C12Q 1/686* (2013.01); *B01F 3/0807* (2013.01); *B01F 5/0085* (2013.01); *B01F 5/0256* (2013.01); *B01F 13/0062* (2013.01); *B01F 13/0071* (2013.01); *B01L 3/502761* (2013.01); *B01L 2200/025* (2013.01); *B01L 2200/0636* (2013.01); *B01L 2200/0647* (2013.01); *B01L 2200/0673* (2013.01); *B01L 2200/14* (2013.01); *B01L 2200/16* (2013.01); *B01L 2300/0609* (2013.01); *B01L 2300/0681* (2013.01); *B01L 2300/0816* (2013.01); *B01L 2300/0829* (2013.01); *B01L 2300/0861* (2013.01); *B01L 2400/049* (2013.01); *G01N 35/08* (2013.01)

(58) Field of Classification Search
  CPC ........... B01L 2200/16; B01L 2200/025; B01L 2300/0681; B01L 2300/0609; B01L 3/502784; B01L 2200/0673; B01L 2300/0816; B01L 3/502761; B01L 2200/0636; B01L 2200/0647; B01L 2300/0861; B01L 3/50273; B01L 3/502; B01L 3/52; B01L 9/527; B01F 3/0807
  See application file for complete search history.

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |

(56) References Cited

U.S. PATENT DOCUMENTS

| | | |
|---|---|---|
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2006/0275893 A1 | 12/2006 | Ishii et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |

(56) References Cited

U.S. PATENT DOCUMENTS

| | | |
|---|---|---|
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1* | 9/2009 | Beer .................... B01F 3/0807 137/3 |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0046243 A1 | 2/2011 | Ito et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0171683 A1 | 7/2012 | Ness et al. |
| 2012/0190032 A1* | 7/2012 | Ness .................... C12Q 1/6806 435/6.12 |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| EP | 1522582 B1 | 4/2007 |
| GB | 1503163 | 3/1978 |
| GB | 2097692 | 11/1982 |
| JP | 0295433 | 4/1990 |
| JP | 10202091 A | 8/1998 |
| JP | 2008080306 A | 4/2008 |
| JP | 2011041925 | 3/2011 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2010036352 A1 | 4/2010 |
| WO | 2011/034621 | 3/2011 |
| WO | 2011/079176 | 6/2011 |
| WO | 2011109546 A1 | 9/2011 |

OTHER PUBLICATIONS

Abate, Adam R. et al., "Functionalized glass coating for PDMS microfluidic devices," Lab on a Chip Technology: Fabrication and Microfluidics, 11 pgs., (2009).

(56) References Cited

OTHER PUBLICATIONS

Abdelgawad, Mohamed et al., "All-terrain droplet actuation," Lab on a Chip, vol. 8, pp. 672-677, Apr. 2, 2008.
Alexandridis, Paschalis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.
Anna, Shelley L. et al., "Formation of dispersions using "flow focusing" in microchannels," Applied Physics Letters, vol. 82, No. 3, Jan. 20, 2003.
Applied Biosystems, "Operator's Manual Tempo Nano LC Tempo NanaTano MDLC Systems", Jan. 1, 2005, 74 pages.
Avilion, Ariel A. et al., "Human Telomerase RNA and Telomerase Activity in Immortal Cell Lines and Tumor Tissues," Cancer Research 56, pp. 645-650, Feb. 1, 1996.
Baroud, Charles N. et al., "Thermocapillary valve for droplet production and sorting," Physical Review E 75, 046302, pp. 046302-1-046302-5, Apr. 5, 2007.
Beer, N. Reginald et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Beer, N. Reginald et al., "On-Chip, Real-Time, Single-Copy Polymerase Chain Reaction in Picoliter Droplets," Analytical Chemistry, vol. 79, No. 22, pp. 8471-8475, Nov. 15, 2007.
Beer, Neil Reginald et al., "Monodisperse droplet generation and rapid trapping for single molecule detection and reaction kinetics measurement," Lab on a Chip, vol. 9, pp. 841-844, Dec. 5, 2008.
Bhat, Somanath et al., "Effect of sustained elevated temperature prior to amplification on template copy number estimation using digital polymerase chain reaction," Analyst, vol. 136, pp. 724-732, (2011).
Blow, Nathan, "PCR's next frontier," Nature Methods, vol. 4, No. 10, pp. 869-875, Oct. 2007.
Bransky, Avishay et al., "A microfluidic droplet generator based on a piezoelectric actuator," Lab on a Chip, vol. 9, pp. 516-520, Nov. 20, 2008.
Carroll, Nick J. et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Cawthon, Richard M., "Telomere length measurement by a novel monochrome multiplex quantitative PCR method," Nucleic Acids Research, vol. 37, No. 3, pp. 1-7, (2009).
Cawthon, Richard M., "Telomere measurement by quantitative PCR," Nucleic Acids Research, vol. 30, No. 10, pp. 1-6, (2002).
Chabert, Max et al., "Droplet fusion by alternating current (AC) field electrocoalescence in microchannels," Electrophoresis, vol. 26, pp. 3706-3715, (2005).
Chen, Chia-Hung et al., "Janus Particles Templated from Double Emulsion Droplets Generated Using Microfluidics," Langmuir, vol. 29, No. 8, pp. 4320-4323, Mar. 18, 2009.
Chen, Delai L. et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
Chittofrati, A. et al., "Perfluoropolyether microemulsions," Progress in Colloid & Polymer Science 79, pp. 218-225, (1989).
Chloroform (Phenomenex), Solvent Miscibility Table, Internet Archive WayBackMachine, 3 pgs., Feb. 1, 2008.
Clausell-Tormos, Jenifer et al., "Droplet-Based Microfluidic Platforms for the Encapsulation and Screening of Mammalian Cells and Multicellular Organisms," Chemistry & Biology, vol. 15, pp. 427-437, May 2008.
Da Rocha, Sandro R. P. et al., "Effect of Surfactants on the Interfacial Tension and Emulsion Formation between Water and Carbon Dioxide," Langmuir, vol. 15, No. 2, pp. 419-428, (1999), published on web Dec. 29, 1998.
Dasgupta, Purnendu K. et al., "Light emitting diode-based detectors Absorbance, fluorescence and spectroelectrochemical measurements in a planar flow-through cell," Analytica Chimica Acta 500, pp. 337-364, (2003).
Diehl, Frank et al., "Digital quantification of mutant DNA in cancer patients," Current Opinion in Oncology, vol. 19, pp. 36-42, (2007).
Diekema, Daniel J. et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Ding, Chunming et al., "Direct molecular haplotyping of long-range genomic DNA with M1-PCR," PNAS, vol. 100, No. 13, pp. 7449-7453, Jun. 24, 2003.
Dorfman, Kevin D. et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
Dressman, Devin et al., "Transforming single DNA molecules into fluorescent magnetic particles for detection and enumeration of genetic variations," PNAS, vol. 100, No. 15, Jul. 22, 2003.
Dube, Simant et al., "Mathematical Analysis of Copy Number Variation in a DNA Sample Using Digital PCR on a Nanofluidic Device," PLoS ONE, vol. 3, Issue 8, pp. 1-9, Aug. 6, 2008.
Eksigent, "Product Note Eksigent: NanoFlow Metering System", Jan. 1, 2010, 4 pages.
Emerson, David et al., "Microfluidic Modelling Activities at C3M," Centre for Microfluidics & Microsystems Modelling, Daresbury Laboratory, pp. 1-26, May 15, 2006.
Eschenback Optik GMBH, Optics for Concentrated Photovoltaics (CPV), 1 pg., date unknown.
Fan, Jian-Bing et al., "Highly parallel genomic assays," Nature Reviews/Genetics, vol. 7, pp. 632-644, Aug. 2006.
Fidalgo, Luis M. et al., "Coupling Microdroplet Microreactors with Mass Spectrometry: Reading the Contents of Single Droplets Online," Angewandte Chemie, vol. 48, pp. 3665-3668, Apr. 7, 2009.
Fielden, Peter et al., "Micro-Droplet Technology for High Throughout Systems and Methods," 1 pg., Mar. 8, 2006.
Garstecki, Piotr et al., "Formation of droplets and bubbles in a microfluidic T-junction—scaling and mechanism of break-up," Lab on a Chip, vol. 6, pp. 437-446, (2006).
Garstecki, Piotr et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Garti, N. et al., "Water Solubilization in Nonionic Microemulsions Stabilized by Grafted Siliconic Emulsifiers," Journal of Colloid and Interface Science vol. 233, pp. 286-294, (2001).
Gasperlin, M. et al., "The structure elucidation of semisolid w/o emulsion systems containing silicone surfactant," International Journal of Pharmaceutics 107, pp. 51-56, (1994).
Ge, Qinyu et al., "Emulsion PCR-based method to detect Y chromosome microdeletions," Analytical Biochemistry, vol. 367, pp. 173-178, May 10, 2007.
Ghenciu, E. G. et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.
Glotsos, Dimitris et al., "Robust Estimation of Bioaffinity Assay Fluorescence Signals," IEEE Transactions on Information Technology in Biomedicine, vol. 10, No. 4, pp. 733-739, Oct. 2006.
Goldschmidt GMBH, "Abil® EM 90 Emulsifier for the formulation of cosmetic W/O creams and lotions," degussa. creating essentials brochure, pp. 1-7, May 2003.
Griffiths, Andrew D. et al., "Miniaturising the laboratory in emulsion droplets," TRENDS in Biotechnology, vol. 24, No. 9, pp. 395-402, Jul. 14, 2006.
Gullberg, Mats et al., "Cytokine detection by antibody-based proximity ligation," PNAS, vol. 101, No. 22, pp. 8420-8424, Jun. 1, 2004.
Guo, Zhen et al., "Enhanced discrimination of single nucleotide polymorphisms by artificial mismatch hybridization," Nature Biotechnology vol. 15, pp. 331-335, Apr. 1997.

(56) References Cited

OTHER PUBLICATIONS

Gustafsdottir, Sigrun M. et al., "In vitro analysis of DNA-protein interactions by proximity ligation," PNAS, vol. 104, No. 9, pp. 3067-3072, Feb. 27, 2007.

Higuchi, Russell et al., "Kinetic PCR Analysis: Real-time Monitoring of DNA Amplification Reactions," Bio/Technology vol. II, pp. 1026-1030, Sep. 11, 1993.

Hill, Randla M., "Silicone surfactants—new developments," Current Opinion in Colloid & Interface Science 7, pp. 255-261, (2002).

Hobbs, Helen R. et al., "Homogeneous Biocatalysis in both Fluorous Biphasic and Supercritical Carbon Dioxide Systems," Angewandte Chemie, vol. 119, pp. 8006-8009, Sep. 6, 2007.

Holtze, C. et al., "Biocompatible surfactants for water-in-fluorocarbon emulsions," Lab on a Chip, vol. 8, pp. 1632-1639, Sep. 2, 2008.

Hori, Machiko et al., "Uniform amplification of multiple DNAs by emulsion PCR," Biochemical and Biophysical Research Communications, vol. 352, pp. 323-328, (2007).

Huang, Jiaqi et al., "Rapid Screening of Complex DNA Samples by Single-Molecule Amplification and Sequencing," PLoS ONE, vol. 6, Issue 5, pp. 1-4, May 2011.

Hung, Lung-Hsin et al., "Rapid microfabrication of solvent-resistant biocompatible microfluidic devices," Lab on a Chip, vol. 8, pp. 983-987, Apr. 8, 2008.

Jarvius, Jonas et al., "Digital quantification using amplified single-molecule detection," Nature Methods, vol. 3, No. 9, pp. 15 pgs, Sep. 2006.

Jin, Dayong et al., "Practical Time-Gated Luminescence Flow Cytometry. II: Experimental Evaluation Using UV LED Excitation," Cytometry Part A • 71A, pp. 797-808, Aug. 24, 2007.

Kalinina, Olga et al., "Nanoliter scale PCR with TaqMan Detection," Nucleic Acids Research, vol. 25, No. 10 pp. 1999-2004, (1997).

Katsura, Shinji et al., "Indirect micromanipulation of single molecules in water-in-oil emulsion," Electrophoresis, vol. 22, pp. 289-293, (2001).

Kekevi, Burcu et al., Synthesis and Characterization of Silicone-Based Surfactants as Anti-Foaming Agents, J. Surfact Deterg (2012), vol. 15, pp. 73-81, published online Jul. 7, 2011.

Kiss, Margaret Macris et al., "High-Throughput Quantitative Polymerase Chain Reaction in Picoliter Droplets," Analytical Chemistry, 8 pgs., downloaded Nov. 17, 2008.

Kumaresan, Palani et al., "High-Throughput Single Copy DNA Amplification and Cell Analysis in Engineered Nanoliter Droplets," Analytical Chemistry, 17 pgs., Apr. 15, 2008.

Kunieda, Hironobu et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Labsmith, "CapTite™ Microfluidic Interconnects" webpage, downloaded Jul. 11, 2012.

Labsmith, "Microfluid Components" webpage, downloaded Jul. 11, 2012.

Landegren, Ulf et al., "Padlock and proximity probes for in situ and array-based analyses: tools for the post-genomic era," Comp. Funct. Genom, vol. 4, pp. 525-530, (2003).

Leamon, John H. et al., "Overview: methods and applications for droplet compartmentalization of biology," Nature Methods, vol. 3, No. 7, pp. 541-543, Jul. 2006.

Lin, Yen-Heng et al., "Droplet Formation Utilizing Controllable Moving-Wall Structures for Double-Emulsion Applications," Journal of Microelectromechanical Systems, vol. 17, No. 3, pp. 573-581, Jun. 2008.

Link, Darren R. et al., "Electric Control of Droplets in Microfluidic Devices," Angewandte Chemie Int. Ed., vol. 45, pp. 2556-2560, (2006).

Liu, Kan et al., "Droplet-based synthetic method using microflow focusing and droplet fusion," Microfluid Nanfluid, vol. 3, pp. 239-243, (2007), published online Sep. 22, 2006.

Lo, Y. M. Dennis et al., "Digital PCR for the molecular detection of fetal chromosomal aneuploidy," PNAS, vol. 104, No. 32, pp. 13116-13121, Aug. 7, 2007.

Luk, Vivienne N. et al., "Pluronic Additives: A Solution to Sticky Problems in Digital Microfluidics," Langmuir, vol. 24, No. 12, pp. 6382-6289, May 16, 2008.

Margulies, Marcel et al., "Genome sequencing in microfabricated high-density picolitre reactors," Nature, vol. 437, 51 pgs., Sep. 15, 2005.

Markey, Amelia L. et al., "High-throughput droplet PCR," Methods, vol. 50, pp. 277-281, Feb. 2, 2010.

Mazutis, Linas et al., "A fast and efficient microfluidic system for highly selective one-to-one droplet fusion," Lab on a Chip, vol. 9, pp. 2665-2672, Jun. 12, 2009.

Mazutis, Linas et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.

McCaughan, Frank et al., "Single-molecule genomics," Journal of Pathology, vol. 220, pp. 297-306, Nov. 19, 2009.

Mehta, Somil C. et a., "Mechanism of Stabilization of Silicone Oil—Water Emulsions Using Hybrid Siloxane Polymers," Langmuir, vol. 24, No. 9, pp. 4558-4563, Mar. 26, 2008.

Mohr, S. et al., "Numerical and experimental study of a droplet-based PCR chip," Microfluid Nanofluid, vol. 3, pp. 611-621, (2007).

Musyanovych, Anna et al., "Miniemulsion Droplets as Single Molecule Nanoreactors for Polymerase Chain Reaction," Biomacromolecules, vol. 6, No. 4, pp. 1824-1828, (2005).

Nagai, Hidenori et al., "Development of a Microchamber Array for Picoliter PCR," Analytical Chemistry, vol. 73, No. 5, pp. 1043-1047, Mar. 1, 2001.

Nam, Yoon Sung et al., "Nanosized Emulsions Stabilized by Semi-solid Polymer Interphase," Langmuir, ACS Publications, Jul. 23, 2010.

Newman, D.A. et al., "Phase Behavior of Fluoroether-Functional Amphiphiles in Supercritical Carbon Dioxide," The Journal of Supercritical Fluids, vol. 6, No. 4, pp. 205-210, (1993).

Nie, Shuming et al., "Optical Detection of Single Molecules," Annu. Rev. Biophys. BiomoL Struct. vol. 26, pp. 567-596, (1997).

O'Lenick, Anthony J. Jr., "Silicone Emulsions and Surfactants," Journal of Surfactants and Detergents, vol. 3, No. 3, Jul. 2000.

O'Lenick, Anthony J., Jr., "Silicone Emulsions and Surfactants—A Review," Silicone Spectator, Silitech LLC, May 2009 (original published May 2000).

Pamme, Nicole, "continuous flow separations in microfluidic devices," Lab on a Chip, vol. 7, pp. 1644-1659, Nov. 2, 2007.

Piatyszek, Mieczyslaw A. et al., "Detection of telomerase activity in human cells and tumors by a telomeric repeat amplification protocol (TRAP)," Methods in Cell Science 17, pp. 1-15, (1995).

Pinheiro, Leonardo B. et al., "Evaluation of a Droplet Digital Polymerase Chain Reaction Format for DNA Copy Number Quantification," Analytical Chemistry, vol. 84, pp. 1003-1011, Nov. 28, 2011.

Pohl, Gudrun et al., "Principle and applications of digital PCR" review, www.future-drugs.com, Expert Rev. Mol. Diagn. 4(1), pp. 41-47, (2004).

Polydimethylsiloxane, 5 pgs., published in FNP 52 (1992).

Price, Christopher B., "Regular Review Point of Care Testing," BMJ, vol. 322, May 26, 2001.

Qin, Jian et al., "Studying copy number variations using a nanofluidic platform," Nucleic Acids Research, vol. 36, No. 18, pp. 1-8, Aug. 18, 2008.

Roach, L. Spencer et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.

Rutledge, R. G. et al., "Mathematics of quantitative kinetic PCR and the application of standard curves," Nucleic Acids Research, vol. 31, No. 16, pp. 1-6, (2003).

Rutledge, R. G., "Sigmoidal curve-fitting redefines quantitative real-time PCR with the prospective of developing automated high-throughput applications," Nucleic Acids Research. vol. 32, No. 22, pp. 1-8, (2004).

(56) References Cited

OTHER PUBLICATIONS

Scherer, A., California Institute of Technology, "Polymerase Chain Reactors" PowerPoint presentation, 24 pgs., date unknown.

Schneegaß, Ivonne et al., "Miniaturized flow-through PCR with different template types in a silicon chip thermocycler," Lab on a Chip, vol. 1, pp. 42-49, (2001).

Schroeder, Groff M. et al., "Introduction to Flow Cytometry" version 5.1, 182 pgs. (2004).

Schütze, Tatjana et al., "A streamlined protocol for emulsion polymerase chain reaction and subsequent purification," Analytical Biochemistry, vol. 410, pp. 155-157, Nov. 25, 2010.

Sela, Y. et al., "Newly designed polysiloxane-graft-poly (oxyethylene) copolymeric surfactants: preparation, surface activity and emulsification properties," Colloid & Polymer Science 272, pp. 684-691, (1994).

Shah, Rhutesh K. et al., "Polymers fit for function Making emulsions drop by drop," Materials Today, vol. 11, No. 4, pp. 18-27, Apr. 2008.

Shendure, Jay et al., "Next-generation DNA sequencing," Nature Biotechnology, vol. 26, No. 10, pp. 1135-1145, Oct. 2008.

Shuber, Anthony P. et al., "A Simplified Procedure for Developing Multiplex PCRs," Genome Research, published by Cold Spring Harbor Laboratory Press, pp. 488-493, (1995).

Sigma-Aldrich, "Synthesis of Mesoporous Materials," Material Matters, 3.1, 17, (2008).

Singley, Edith J. et al., "Phase behavior and emulsion formation of novel fluoroether amphiphiles in carbon dioxide," Fluid Phase Equilibria 128, pp. 199-219, (1997).

Smid-Korbar, J. et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.

Snow, Steven A. "Synthesis and Characterization of Zwitterionic Silicone Sulfobetaine Surfactants," Langmuir, vol. 6, No. 2, American Chemical Society, pp. 385-391, (1990).

Solimini, Nicole L. et al., "Recurrent Hemizygous Deletions in Cancers May Optimize Proliferative Potential," Science, vol. 337, pp. 104-109, Jul. 6, 2012.

Swillens, Stéphane et al., "Instant evaluation of the absolute initial number of cDNA copies from a single real-time PCR curve," Nucleic Acids Research, vol. 32, No. 6, pp. 1-6, (2004).

Tan, Yung-Chieh et al., "Monodispersed microfluidic droplet generation by shear focusing microfluidic device", Sensors and Actuators B, vol. 114 (2006) pp. 350-356.

Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).

Tanner, Nathan A. et al., "Simultaneous multiple target detection in real-time loop-mediated isothermal amplification," BioTechniques, vol. 53, pp. 8-19, Aug. 2012.

The, Shia-Yen et al., "Droplet microfluidics," Lab on a Chip, vol. 8, pp. 198-220, Jan. 11, 2008.

Thinxxs Microtechnology AG, "Emerald Biosystems: Protein Crystallization," 1 pg., downloaded Mar. 8, 2011.

Thurecht, Kristofer J. et al., "Investigation of spontaneous microemulsion formation in supercritical carbon dioxide using high-pressure NMR," Journal of Supercritical Fluids, vol. 38, pp. 111-118, (2006).

Thurecht, Kristofer J. et al., "Kinetics of Enzymatic Ring-Opening Polymerization of ∈-Caprolactone in Supercritical Carbon Dioxide," Macromolecules, vol. 39, pp. 7967-7972, (2006).

Vogelstein, Bert et al., "Digital PCR," Proc. Natl. Acad. Sci. USA, vol. 96, pp. 9236-9241, Aug. 1999.

Vulto, Paul et al., "Phaseguides: a paradigm shift in microfluidic priming and emptying," Lab on a Chip, vol. 11, No. 9, pp. 1561-1700, May 7, 2011.

Wang, Anfeng et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Weaver, Suzanne et al., "Taking qPCR to a higher level: Analysis of CNV reveals the power of high throughput qPCR to enhance quantitative resolution," Methods, vol. 50, pp. 271-276, Jan. 15, 2010.

Weitz, David A., "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.

Wetmur, James G. et al., "Molecular haplotyping by linking emulsion PCR: analysis of paraoxonase 1 haplotypes and phenotypes," Nucleic Acids Research, vol. 33, No. 8, pp. 2615-2619, (2005).

Wetmur, James G., et al., "Linking Emulsion PCR Haplotype Analysis," PCR Protocols, Methods in Molecular Biology, vol. 687, pp. 165-175, (2011).

Williams, Richard et al., "Amplification of complex gene libraries by emulsion PCR," Nature Methods, vol. 3, No. 7, pp. 545-550, Jul. 2006.

Yazdi, A. V. et al., "Highly Carbon Dioxide Soluble Surfactants, Dispersants and Chelating Agents," Fluid Phase Equilibria, vol. 117, pp. 297-303, (1996).

Zhang, Chunsun et al., "Miniaturized PCR chips for nucleic acid amplification and analysis: latest advances and future trends," Nucleic Acids Research, vol. 35, No. 13, pp. 4223-4237, Jun. 18, 2007.

Zhang, Tianhao et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.

Zhao, Yuejun et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.

Zhelev, Toshko et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).

Zhong, Qun et al., "Multiplex digital PCR: breaking the one target per color barrier of quantitative PCR," Lab on a Chip, vol. 11, pp. 2167-2174, (2011).

Zimmermann, Bernhard G. et al., "Digital PCR: a powerful new tool for noninvasive prenatal diagnosis?," Prenatal Diagnosis, vol. 28 pp. 1087-1093, Nov. 10, 2008.

Kriwet, Burkhard et al., "Synthesis of bioadhesive poly(acrylic acid) nano- and microparticles using an inverse emulsion polymerization method for the entrapment of hydrophilic drug candidates", Journal of Controlled Release, vol. 56, No. 1-3, pp. 149-158, Dec. 4, 1998.

European Patent Office, "Extended Search Report" in connection with related European Patent Application No. 16190414.9, 10 pages, Jan. 19, 2017.

Naeye, B. et al., "PEGylation of biodegradable dextran nanogels for siRNA delivery", European Journal of Pharmaceutical Sciences, vol. 40, No. 4 pp. 342-351, Apr. 16, 2010.

Princen, H. M., "Highly Concentrated Emulsions, I. Cylindrical Systems", Analytical Sciences, The Japan Society for Analytical Chemistry, US, vol. 71, No. 1, pp. 55-56, Aug. 1, 1979.

\* cited by examiner

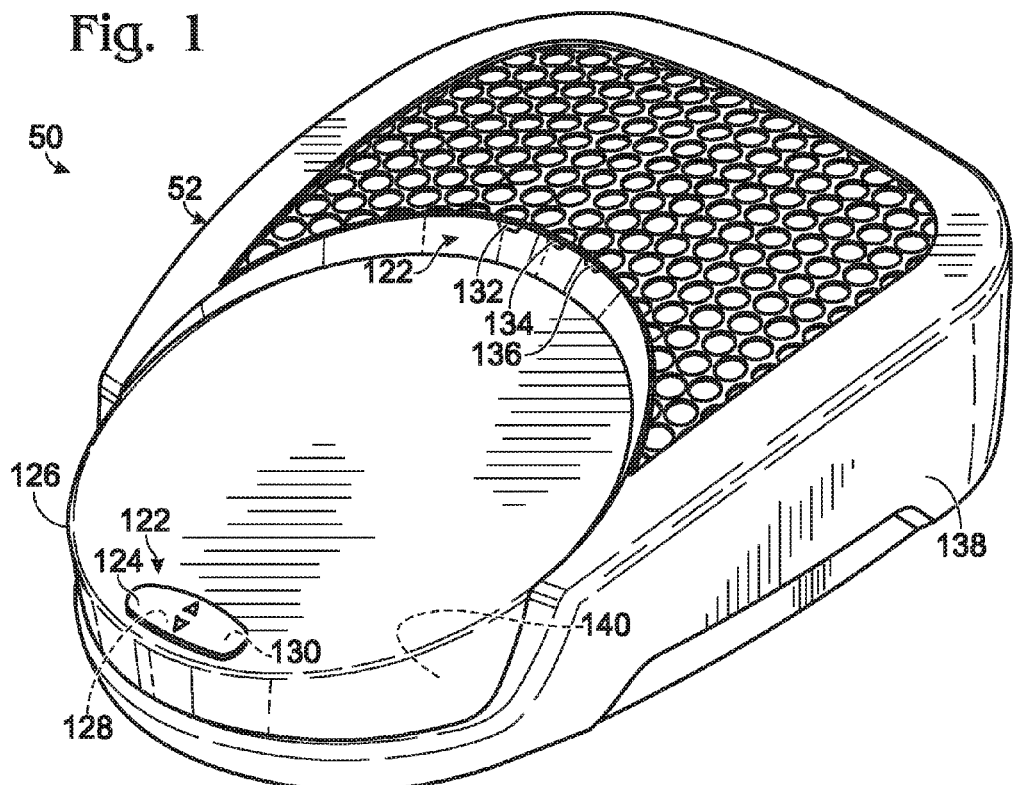
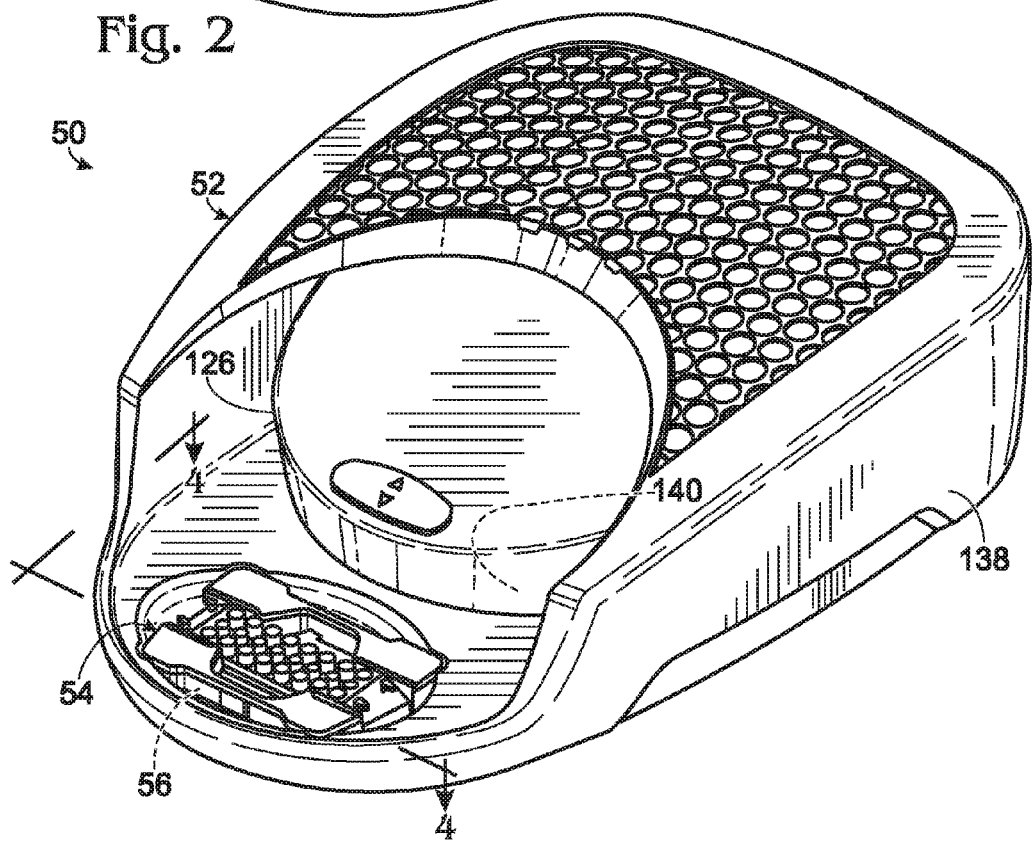

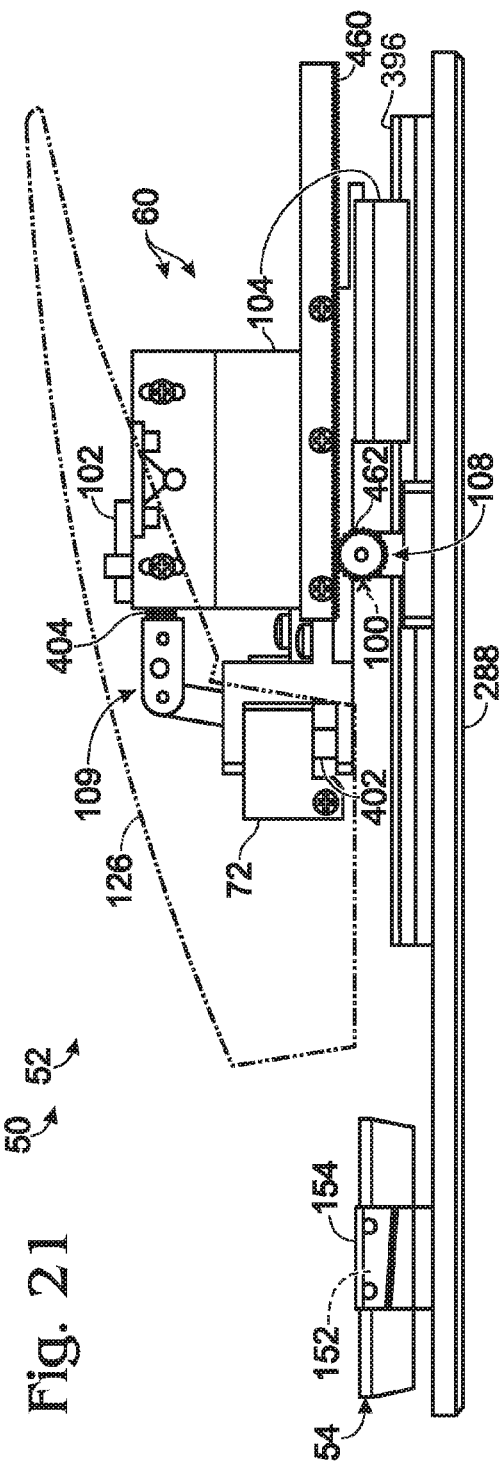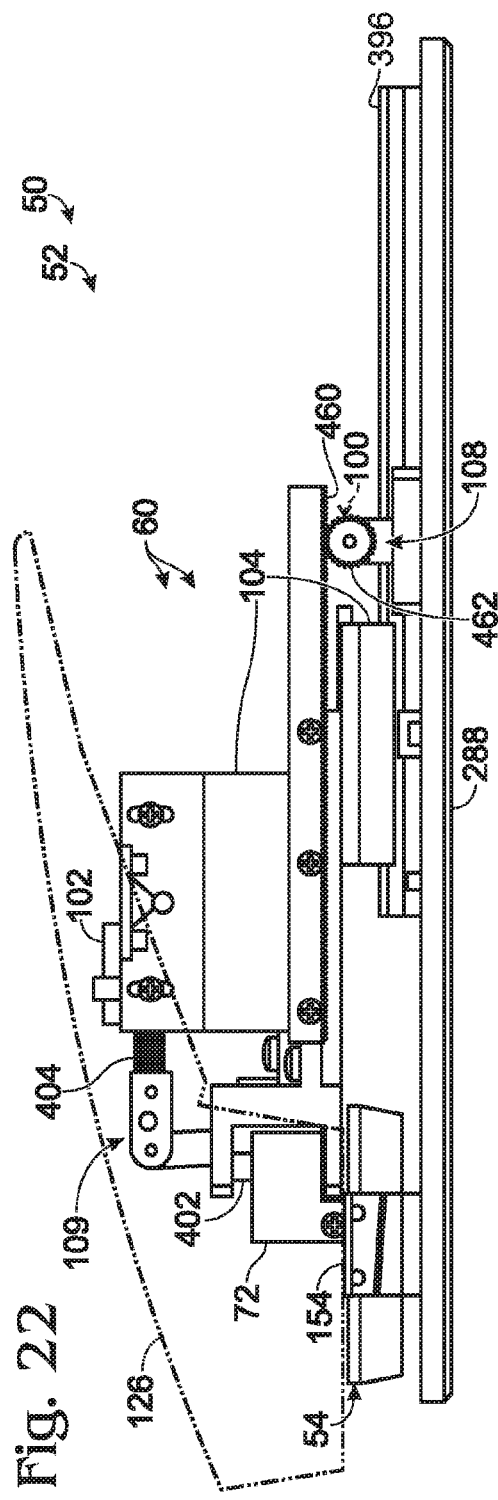

SYSTEM FOR GENERATING DROPLETS WITH PRESSURE MONITORING

CROSS-REFERENCES TO PRIORITY APPLICATIONS

This application is a continuation-in-part of the following U.S. patent applications: Ser. No. 12/954,634, filed Nov. 25, 2010; Ser. No. 13/400,030, filed Feb. 17, 2012; Ser. No. 14/020,742, filed Sep. 6, 2013; Ser. No. 14/159,410, filed Jan. 20, 2014, now U.S. Pat. No. 9,492,797; Ser. No. 14/201,752 filed Mar. 7, 2014; and Ser. No. 14/848,311, filed Sep. 8, 2015.

U.S. patent application Ser. No. 14/159,410, in turn, is a continuation-in-part of the following patent applications: Ser. No. 12/586,626, filed Sep. 23, 2009, now U.S. Pat. No. 9,156,010; Ser. No. 12/862,542, filed Aug. 24, 2010, now U.S. Pat. No. 9,194,861; Ser. No. 12/890,550, filed Sep. 24, 2010, now U.S. Pat. No. 8,633,015; Ser. No. 13/245,575, filed Sep. 26, 2011, now abandoned; Ser. No. 13/945,661, filed Jul. 18, 2013, now U.S. Pat. No. 9,417,190; Ser. No. 12/962,507, filed Dec. 7, 2010, now U.S. Pat. No. 9,216,392; Ser. No. 12/962,511, filed Dec. 7, 2010; Ser. No. 12/962,502, filed Dec. 7, 2010, now U.S. Pat. No. 9,248,417; Ser. No. 12/963,523, filed Dec. 8, 2010, now U.S. Pat. No. 9,126,160; Ser. No. 13/039,233, filed Mar. 2, 2011, now U.S. Pat. No. 8,709,762; Ser. No. 12/976,827, filed Dec. 22, 2010; Ser. No. 13/341,669, filed Dec. 30, 2011, now U.S. Pat. No. 9,500,664; Ser. No. 13/341,678, filed Dec. 30, 2011, now U.S. Pat. No. 8,730,479; Ser. No. 13/072,673, filed Mar. 25, 2011, now U.S. Pat. No. 9,132,394; Ser. No. 13/341,688, filed Dec. 30, 2011, now U.S. Pat. No. 9,393,560; Ser. No. 13/287,120, filed Nov. 1, 2011, now U.S. Pat. No. 9,089,844; Ser. No. 13/424,304, filed Mar. 19, 2012, now U.S. Pat. No. 9,222,128; Ser. No. 13/548,062, filed Jul. 12, 2012, now U.S. Pat. No. 8,951,939; Serial No. PCT/US2012/048198, filed Jul. 25, 2012; Ser. No. 13/562,198, filed Jul. 30, 2012, now U.S. Pat. No. 8,663,920; Ser. No. 13/287,095, filed Nov. 1, 2011; and Ser. No. 13/863,231, filed Apr. 15, 2013, now U.S. Pat. No. 9,399,215.

U.S. patent application Ser. No. 12/586,626, in turn, is based upon and claims the benefit under 35 U.S.C. §119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009.

U.S. patent application Ser. No. 12/862,542, in turn, is based upon and claims the benefit under 35 U.S.C. §119(e) of U.S. Provisional Patent Application Ser. No. 61/275,860, filed Sep. 2, 2009.

U.S. patent application Ser. No. 12/890,550, in turn, is a continuation-in-part of U.S. patent application Ser. No. 12/586,626, filed Sep. 23, 2009, now U.S. Pat. No. 9,156,010, which, in turn, claims priority to further applications as listed above.

U.S. patent application Ser. No. 13/245,575, in turn, is a continuation of U.S. patent application Ser. No. 12/586,626, filed Sep. 23, 2009, now U.S. Pat. No. 9,156,010, which, in turn, claims priority to further applications as listed above.

U.S. patent application Ser. No. 13/945,661, in turn, is a continuation-in-part of the following U.S. patent applications: Ser. No. 13/251,016, filed Sep. 30, 2011, now abandoned; Ser. No. 13/245,575, filed Sep. 26, 2011, now abandoned; and Ser. No. 12/976,827, filed Dec. 22, 2010, the latter two of which, in turn, claim priority to further applications as listed elsewhere in this section.

U.S. patent application Ser. No. 12/962,507, in turn, is a continuation of U.S. patent application Ser. No. 12/586,626, filed Sep. 23, 2009, now U.S. Pat. No. 9,156,010, which, in turn, claims priority to further applications as listed above.

U.S. patent application Ser. No. 12/962,511, in turn, is a continuation of U.S. patent application Ser. No. 12/586,626, filed Sep. 23, 2009, now U.S. Pat. No. 9,156,010, which, in turn, claims priority to further applications as listed above.

U.S. patent application Ser. No. 12/962,502, in turn, is a continuation of U.S. patent application Ser. No. 12/586,626, filed Sep. 23, 2009, now U.S. Pat. No. 9,156,010, which, in turn, claims priority to further applications as listed above.

U.S. patent application Ser. No. 12/963,523, in turn, is a continuation of U.S. patent application Ser. No. 12/586,626, filed Sep. 23, 2009, now U.S. Pat. No. 9,156,010, which, in turn, claims priority to further applications as listed above.

U.S. patent application Ser. No. 13/039,233, in turn, is based upon and claims the benefit under 35 U.S.C. §119(e) of U.S. Provisional Patent Application Ser. No. 61/309,837, filed Mar. 2, 2010.

U.S. patent application Ser. No. 12/976,827, in turn, is based upon and claims the benefit under 35 U.S.C. §119(e) of the following U.S. provisional patent applications: Ser. No. 61/309,845, filed Mar. 2, 2010; Ser. No. 61/341,218, filed Mar. 25, 2010; Ser. No. 61/317,635, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; Ser. No. 61/410,769, filed Nov. 5, 2010; and Ser. No. 61/417,241, filed Nov. 25, 2010.

U.S. patent application Ser. No. 13/341,669, in turn, is a continuation of PCT Patent Application Serial No. PCT/US2011/030101, filed Mar. 25, 2011, which, in turn, is based upon and claims the benefit under 35 U.S.C. §119(e) of U.S. Provisional Patent Application Ser. No. 61/341,218, filed Mar. 25, 2010.

U.S. patent application Ser. No. 13/341,678, in turn, is a continuation of PCT Patent Application Serial No. PCT/US2011/030077, filed Mar. 25, 2011, which, in turn, claims the benefit under 35 U.S.C. §119(e) of U.S. Provisional Patent Application Ser. No. 61/317,684, filed Mar. 25, 2010.

U.S. patent application Ser. No. 13/072,673, in turn, is based upon and claims the benefit under 35 U.S.C. §119(e) of U.S. Provisional Patent Application Ser. No. 61/317,635, filed Mar. 25, 2010, and U.S. Provisional Patent Application Ser. No. 61/467,347, filed Mar. 24, 2011, and is a continuation-in-part of U.S. patent application Ser. No. 12/586,626, filed Sep. 23, 2009, now U.S. Pat. No. 9,156,010, which, in turn, claims priority to further applications as listed above.

U.S. patent application Ser. No. 13/341,688, in turn, is a continuation of PCT Patent Application Serial No. PCT/US2011/030097, filed Mar. 25, 2011, which, in turn, claims the benefit under 35 U.S.C. §119(e) of the following U.S. provisional patent applications: Ser. No. 61/341,065, filed Mar. 25, 2010; and Ser. No. 61/467,347, filed Mar. 24, 2011.

U.S. patent application Ser. No. 13/287,120, in turn, is based upon and claims the benefit under 35 U.S.C. §119(e) of the following U.S. provisional patent applications: Ser. No. 61/409,106, filed Nov. 1, 2010; Ser. No. 61/409,473, filed Nov. 2, 2010; and Ser. No. 61/410,769, filed Nov. 5, 2010.

U.S. patent application Ser. No. 13/424,304, in turn, is based upon and claims the benefit under 35 U.S.C. §119(e) of U.S. Provisional Patent Application Ser. No. 61/454,373, filed Mar. 18, 2011.

U.S. patent application Ser. No. 13/548,062, in turn, is based upon and claims the benefit under 35 U.S.C. §119(e) of the following U.S. provisional patent applications: Ser. No. 61/507,082, filed Jul. 12, 2011; and Ser. No. 61/510,013, filed Jul. 20, 2011.

PCT Patent Application Serial No. PCT/US2012/048198, in turn, is based upon and claims the benefit under 35 U.S.C. §119(e) of U.S. Provisional Patent Application Ser. No. 61/511,445, filed Jul. 25, 2011.

U.S. patent application Ser. No. 13/562,198, in turn, is based upon and claims the benefit under 35 U.S.C. §119(e) of the following U.S. provisional patent applications: Ser. No. 61/513,474, filed Jul. 29, 2011; and Ser. No. 61/601,514, filed Feb. 21, 2012.

U.S. patent application Ser. No. 13/287,095, in turn, is continuation-in-part of U.S. patent application Ser. No. 12/976,827, filed Dec. 22, 2010, which, in turn, claims priority to further applications as listed above.

U.S. patent application Ser. No. 13/863,231, in turn, is based upon and claims the benefit under 35 U.S.C. §119(e) of U.S. Provisional Patent Application Ser. No. 61/624,199, filed Apr. 13, 2012.

U.S. patent application Ser. No. 12/954,634, in turn, is based upon and claims the benefit under 35 U.S.C. §119(e) of the following U.S. provisional patent applications: Ser. No. 61/264,591, filed Nov. 25, 2009; Ser. No. 61/309,845, filed Mar. 2, 2010; Ser. No. 61/309,837, filed Mar. 2, 2010; Ser. No. 61/317,684, filed Mar. 25, 2010; Ser. No. 61/317,635, filed Mar. 25, 2010; Ser. No. 61/317,639, filed Mar. 25, 2010; Ser. No. 61/341,065, filed Mar. 25, 2010; Ser. No. 61/341,218, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; and Ser. No. 61/410,769, filed Nov. 5, 2010.

U.S. patent application Ser. No. 13/400,030, in turn, is based upon and claims the benefit under 35 U.S.C. §119(e) of the following U.S. provisional patent applications: Ser. No. 61/444,674, filed Feb. 18, 2011; Ser. No. 61/449,580, filed Mar. 4, 2011; Ser. No. 61/453,537, filed Mar. 16, 2011; Ser. No. 61/478,777, filed Apr. 25, 2011; Ser. No. 61/488,667, filed May 20, 2011; and Ser. No. 61/490,040, filed May 25, 2011.

U.S. patent application Ser. No. 14/020,742, in turn, is based upon and claims the benefit under 35 U.S.C. §119(e) of U.S. Provisional Patent Application Ser. No. 61/697,982, filed Sep. 7, 2012.

U.S. patent application Ser. No. 14/201,752, in turn, is based upon and claims the benefit under 35 U.S.C. §119(e) of U.S. Provisional Patent Application Ser. No. 61/775,415, filed Mar. 8, 2013.

U.S. patent application Ser. No. 14/848,311, in turn, is a divisional of U.S. patent application Ser. No. 13/385,277, filed Feb. 9, 2012, which issued Sep. 8, 2015 as U.S. Pat. No. 9,127,312; which application claims the benefit of the following U.S. provisional patent applications: Ser. No. 61/441,209, filed Feb. 9, 2011; Ser. No. 61/444,539, filed Feb. 18, 2011; Ser. No. 61/454,373, filed Mar. 18, 2011; Ser. No. 61/476,115, filed Apr. 15, 2011; Ser. No. 61/478,777, filed Apr. 25, 2011; Ser. No. 61/484,197, filed May 9, 2011; and Ser. No. 61/490,055, filed May 25, 2011.

Each of these priority documents is incorporated herein by reference in its entirety for all purposes.

CROSS-REFERENCES TO MATERIALS INCORPORATED BY REFERENCE

This application incorporates by reference in its entirety for all purposes U.S. Pat. No. 7,041,481, issued May 9, 2006.

This application incorporates by reference in their entireties for all purposes the following U.S. patent applications: Ser. No. 12/586,626, filed Sep. 23, 2009; Ser. No. 12/862,542, filed Aug. 24, 2010; Ser. No. 12/890,550, filed Sep. 24, 2010; Ser. No. 12/962,502, filed Dec. 7, 2010; Ser. No. 12/962,507, filed Dec. 7, 2010; Ser. No. 12/962,511, filed Dec. 7, 2010; Ser. No. 12/963,523, filed Dec. 8, 2010; Ser. No. 12/976,827, filed Dec. 22, 2010; Ser. No. 13/039,233, filed Mar. 2, 2011; Ser. No. 13/072,673, filed Mar. 25, 2011; Ser. No. 13/245,575, filed Sep. 26, 2011; Ser. No. 13/250,815, filed Sep. 30, 2011; Ser. No. 13/251,016, filed Sep. 30, 2011; Ser. No. 13/287,095, filed Nov. 1, 2011; Ser. No. 13/287,120, filed Nov. 1, 2011; Ser. No. 13/341,669, filed Dec. 30, 2011; Ser. No. 13/341,678, filed Dec. 30, 2011; Ser. No. 13/341,688, filed Dec. 30, 2011; Ser. No. 13/424,304, filed Mar. 19, 2012; Ser. No. 13/548,062, filed Jul. 12, 2012; Ser. No. 13/549,360, filed Jul. 13, 2012; Ser. No. 13/562,198, filed Jul. 30, 2012; Ser. No. 13/603,235, filed Sep. 4, 2012; Ser. No. 13/863,231, filed Apr. 15, 2013; Ser. No. 13/945,661, filed Jul. 18, 2013; Ser. No. 13/949,115, filed Jul. 23, 2013; Ser. No. 13/973,940, filed Aug. 22, 2013; Ser. No. 14/032,149, filed Sep. 19, 2013; Ser. No. 14/054,698, filed Oct. 15, 2013; and Ser. No. 14/099,750, filed Dec. 6, 2013.

This application incorporates by reference in their entireties for all purposes the following PCT patent applications: Serial No. PCT/US2011/030077, filed Mar. 25, 2011; Serial No. PCT/US2011/030097, filed Mar. 25, 2011; Serial No. PCT/US2011/030101, filed Mar. 25, 2011; and Serial No. PCT/US2012/048198, filed Jul. 25, 2012.

This application incorporates by reference in their entireties for all purposes the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/275,860, filed Sep. 2, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; Ser. No. 61/277,270, filed Sep. 22, 2009; Ser. No. 61/309,837, filed Mar. 2, 2010; Ser. No. 61/309,845, filed Mar. 2, 2010; Ser. No. 61/317,635, filed Mar. 25, 2010; Ser. No. 61/317,684, filed Mar. 25, 2010; Ser. No. 61/341,065, filed Mar. 25, 2010; Ser. No. 61/341,218, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; Ser. No. 61/410,769, filed Nov. 5, 2010; Ser. No. 61/417,241, filed Nov. 25, 2010; Ser. No. 61/454,373, filed Mar. 18, 2011; Ser. No. 61/467,347, filed Mar. 24, 2011; Ser. No. 61/507,560, filed Jul. 13, 2011; Ser. No. 61/507,082, filed Jul. 12, 2011; Ser. No. 61/510,013, filed Jul. 20, 2011; Ser. No. 61/511,445, filed Jul. 25, 2011; Ser. No. 61/513,474, filed Jul. 29, 2011; Ser. No. 61/530,340, filed Sep. 1, 2011; Ser. No. 61/601,514, filed Feb. 21, 2012; Ser. No. 61/624,199, filed Apr. 13, 2012; Ser. No. 61/674,516, filed Jul. 23, 2012; Ser. No. 61/692,635, filed Aug. 23, 2012; Ser. No. 61/703,200, filed Sep. 19, 2012; Ser. No. 61/714,033, filed Oct. 15, 2012; Ser. No. 61/734,296, filed Dec. 6, 2012; Ser. No. 61/759,775, filed Feb. 1, 2013;

This application incorporates by reference in its entirety for all purposes Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples. For example, in research and clinical applications, high-throughput genetic tests using target-specific reagents can provide accurate and precise quantification of nucleic acid targets for drug discovery, biomarker discovery, and clinical diagnostics, among others.

Emulsions hold substantial promise for revolutionizing high-throughput assays. Emulsification techniques can create large numbers of aqueous droplets that function as independent reaction chambers for biochemical reactions. For example, an aqueous sample (e.g., 20 microliters) can be partitioned into droplets (e.g., 20,000 droplets of one nanoliter each) to allow an individual test to be performed on each of the droplets.

Aqueous droplets can be suspended in oil to create a water-in-oil emulsion (W/O). The emulsion can be stabilized with a surfactant to reduce coalescence of droplets during heating, cooling, and transport, thereby enabling thermal cycling to be performed. Accordingly, emulsions have been used to perform single-copy amplification of nucleic acid target molecules in droplets using the polymerase chain reaction (PCR). Digital assays are enabled by the ability to detect the presence of individual molecules of a target in droplets.

In an exemplary droplet-based digital assay, a sample is partitioned into a set of droplets at a limiting dilution of a target (i.e., some of the droplets contain no molecules of the target). If molecules of the target are distributed randomly among the droplets, the probability of finding exactly 0, 1, 2, 3, or more target molecules in a droplet, based on a given average concentration of the target in the droplets, is described by a Poisson distribution. Conversely, the concentration of target molecules in the droplets (and thus in the sample) may be calculated from the probability of finding a given number of molecules in a droplet.

Estimates of the probability of finding no target molecules and of finding one or more target molecules may be measured in the digital assay. In a binary approach, each droplet can be tested to determine whether the droplet is positive and contains at least one molecule of the target, or is negative and contains no molecules of the target. The probability of finding no molecules of the target in a droplet can be approximated by the fraction of droplets tested that are negative (the "negative fraction"), and the probability of finding at least one target molecule by the fraction of droplets tested that are positive (the "positive fraction"). The positive fraction or the negative fraction then may be utilized in a Poisson algorithm to calculate the concentration of the target in the droplets. In other cases, the digital assay may generate data that is greater than binary. For example, the assay may measure how many molecules of the target are present in each droplet with a resolution greater than negative (0) or positive (>0) (e.g., 0, 1, or >1 molecules; 0, 1, 2, or >2 molecules; or the like).

The promise of emulsification to revolutionize biomedical assays requires an efficient system for forming emulsions. However, available systems may not use samples efficiently—a substantial portion of the sample may not be incorporated into the emulsion and instead may be wasted rather than tested. Also, the systems may not be automated at all or at least not sufficiently to free the user for other tasks during emulsion formation. In some cases, the systems may fail to be user-friendly by requiring substantial skill and training to operate successfully. Furthermore, the systems may not provide adequate safeguards to minimize cross-contamination of samples.

A better system for forming emulsions is needed.

SUMMARY

The present disclosure provides a system, including methods, apparatus, and kits, for forming emulsions. In an exemplary method of generating droplets, a device may be selected that includes a plurality of emulsion-formation units each including a sample well, a continuous-phase well, a droplet well, and a channel network that fluidically interconnects the wells and creates a droplet-generation region. A discrete volume of sample-containing fluid may be placed into the sample well of each emulsion-formation unit, and a discrete volume of continuous-phase fluid into the continuous-phase well of each emulsion-formation unit. Pressure may be applied to the device with a fluidics assembly after the step of placing, such that the plurality of emulsion-formation units generate droplets in parallel with one another. A pressure signal may be detected from the fluidics assembly. Application of the pressure may be stopped when the pressure signal indicates that a sample well is empty.

BRIEF DESCRIPTION OF THE DRAWINGS

FIG. 1 is a view of an exemplary system for forming emulsions that includes an instrument that functions as an emulsification engine, with the instrument in a closed configuration, in accordance with aspects of the present disclosure.

FIG. 2 is another view of the system of FIG. 1 with the instrument in an open configuration that reveals a microfluidic cassette seated in a receiving area of the instrument, in accordance with aspects of the present disclosure.

FIG. 21 is a side view of selected aspects of the system of FIGS. 1 and 2, taken with the manifold in a retracted and raised configuration that permits the cassette to be loaded into and removed from the instrument, in accordance with aspects of the present disclosure.

FIG. 22 is a side view of selected aspects of the system of FIGS. 1 and 2, taken as in FIG. 21 but with the manifold in an extended and lowered configuration in which the manifold is operatively engaged with the cassette, in accordance with aspects of the present disclosure.

DETAILED DESCRIPTION

Figure 3:
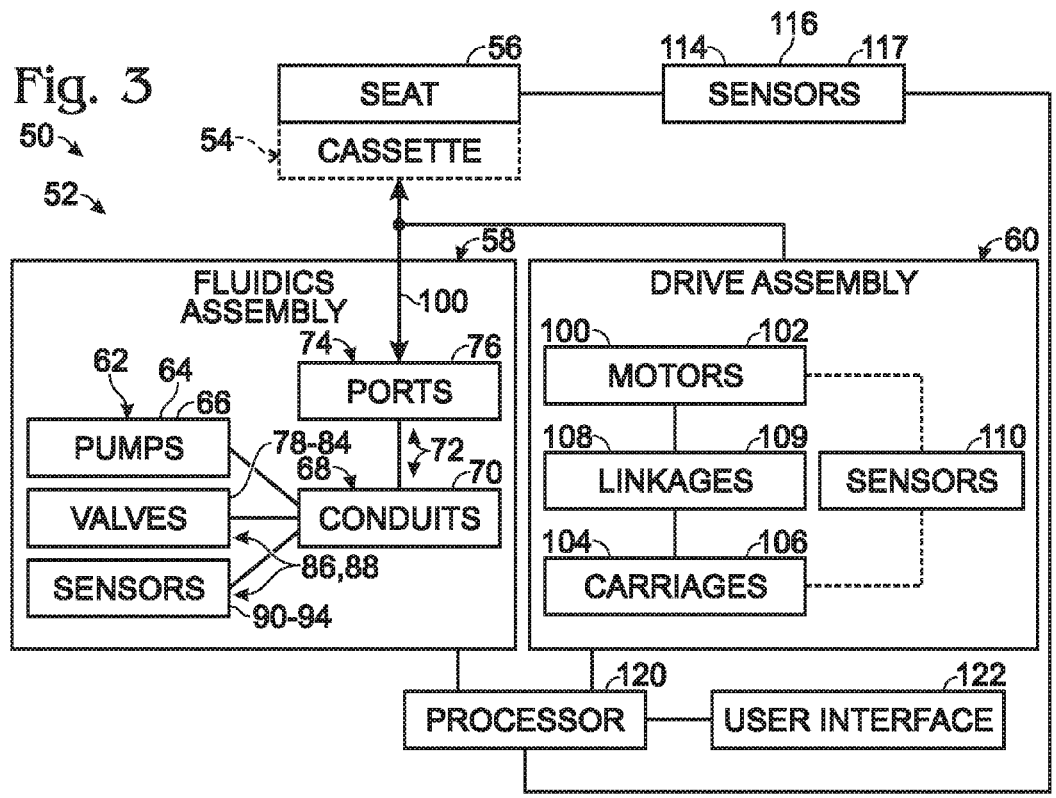
FIG. 3 is a schematic view of the system of FIGS. 1 and 2.

The present disclosure provides a system, including methods, apparatus, and kits, for forming emulsions. The system may include an instrument and a microfluidic chip received by the instrument. The instrument may apply pressure to prospective emulsion phases held by the chip, to drive formation and collection of emulsions in the chip. In some embodiments, the instrument may stop applying pressure to the chip when a change in pressure meeting a predefined condition is detected by the instrument. The change may indicate that an endpoint of droplet generation has been reached.

An exemplary method of emulsion formation is provided. In the method, pressure may be applied to a microfluidic chip holding prospective emulsion phases, to drive droplet formation and collection of emulsions in the chip. The pressure may be monitored for a change that meets a predefined condition. Application of the pressure may be stopped when the change is detected.

Another exemplary method of emulsion formation is provided. In the method, pressure may be applied to a microfluidic chip holding prospective emulsion phases in input containers, to drive the phases through channels of the chip for droplet formation and collection as emulsions in output containers of the chip. Application of the pressure may be stopped after air has followed liquid into one or more of the channels from one or more of the input containers and before a significant volume of air enters the output containers, such as before the air has reached all of the emulsions collected in the output containers.

Yet another exemplary method of emulsion formation is provided. In the method, pressure may be applied to a microfluidic chip holding samples and at least one continuous phase, to drive formation of droplets and collection of emulsions in the chip. Application of the pressure may be stopped when at least about 80% by volume of each of the samples has been converted to droplets.

Still another exemplary method of emulsion formation is provided. In the method, prospective emulsions phases may be dispensed into wells of a microfluidic chip. The chip may be disposed in a receiving area of an instrument. An actuation signal may be inputted to the instrument. The actuation signal may cause the instrument to apply pressure to the chip to drive formation and collection of emulsions in parallel in the chip, and to stop application of pressure when an endpoint of emulsion formation has been reached.

Yet still another exemplary method of emulsion formation is provided. In the method, pressure may be applied to a microfluidic chip holding prospective emulsion phases, to drive droplet formation and collection of emulsions in the chip. Monitoring may be performed with at least one sensor. The sensor may monitor an aspect of liquid held by the chip and/or of a fluid volume in contact with the liquid for a change that indicates an endpoint for droplet generation has been reached. Application of the pressure may be stopped when the change is detected.

Still yet another exemplary method of emulsion formation is provided. In the method, a first phase and an immiscible second phase may be driven through a droplet generator and forward along a flow path connecting the droplet generator to a container, such that an emulsion of first phase droplets disposed in the second phase is collected in the container. The emulsion may be concentrated. For example, a volume fraction of the second phase in the collected emulsion may be decreased by selectively driving the second phase from the container in reverse along the flow path.

Yet another exemplary method of emulsion formation is provided. In the method, negative or positive gas pressure may be established in a reservoir. Fluid communication may be created between the reservoir and a microfluidic chip holding prospective emulsion phases. The fluid communication may be maintained while the established pressure drives droplet formation and collection of emulsions in the chip, without modification of the established pressure by a pump.

Another exemplary method of emulsion formation is provided. In the method, a first microfluidic chip and a first gasket defining a plurality of orifices may be disposed in a receiving area of an instrument, with the first gasket connected to the first chip. Pressure may be applied with an instrument to the first microfluidic chip via the orifices to drive droplet formation and collection of emulsions in the first chip. The first chip and the first gasket may be removed from the receiving area. Disposing, applying, and removing may be repeated with a second microfluidic chip and a second gasket, or the first chip and/or first gasket may be reused.

An exemplary system for emulsion formation is provided. The system may comprise a microfluidic chip configured to hold prospective emulsion phases. The system also may comprise an instrument including a fluidics assembly having a pressure sensor. The instrument may be configured to apply pressure to the chip with the fluidics assembly to drive droplet generation and collection of emulsions in the chip. The instrument also may be configured to monitor the pressure with the pressure sensor for a change indicating an endpoint of droplet generation has been reached, and to stop application of the pressure when the change is detected by the pressure sensor.

An exemplary kit is provided for use with an instrument. The kit may include any combination of one or more microfluidic chips, one or more gaskets, one or more cartridges to hold the chips and/or gaskets, a volume of continuous phase disposed in a container and sufficient for forming a plurality of emulsions in a chip, reagents for addition to aqueous samples to enable emulsification and/or an amplification reaction, and instructions for using kit components with the instrument for driving emulsion formation in a chip, among others.

The emulsion formation system disclosed herein has substantial advantages over other approaches to forming emulsions. The advantages may include (1) more complete incorporation of each sample into an emulsion (i.e., less sample is wasted), (2) the ability to concentrate each emulsion by reverse flow of the continuous phase after emulsion collection, (3) single-step actuation of the instrument after loading the chip, (4) sample containment by a chip and a gasket that are both disposable, (5) a removable and reusable cartridge for holding the chip and the gasket, (6) the ability to monitor flow and/or pressure within a range or about a set point to make it possible to deliver monodisperse emulsions and/or highly uniform volumes of dispersed and continuous phases, or any combination thereof, among others.

These and other aspects of the present disclosure are described in the following sections: (I) overview of an exemplary emulsion formation system with an instrument and a cassette, (II) an exemplary cassette, (III) an exemplary microfluidic chip, (IV) exemplary cartridge, (V) exemplary seated configuration for a cassette in the instrument, (VI) exemplary structure and operation of a fluidics assembly for the instrument, (VII) exemplary structure and operation of a drive assembly for the instrument, and (VIII) selected embodiments.

I. Overview of an Exemplary Emulsion Formation System with an Instrument and a Cassette This section describes an exemplary emulsion formation system 50 including an instrument 52 and a microfluidic cassette 54; see FIGS. 1 to 3.

FIGS. 1 and 2 show instrument 52 in respective closed and open configurations. The instrument may be described as an emulsification engine or apparatus that drives any combination of fluid flow, droplet generation, emulsion formation, emulsion collection, and emulsion concentration, among others, in cassette 54. The instrument may form a seat 56 (interchangeably termed a seating area, a receiving area, or a loading site) at which the cassette may be operatively disposed for interaction with the instrument.

FIG. 3 shows a schematic view of instrument 52 and cassette 54 of system 50, with cassette 54 engaged with seat 56. Instrument 52 may be equipped with a fluidics assembly 58 and a drive assembly 60. Fluidics assembly 58 may be any mechanism or set of mechanisms that, among others, contains, releases, directs, drives, monitors, regulates, controls, and/or detects fluid, generally, gas and/or liquid, in instrument 52 and cassette 54. Drive assembly 60 may be any mechanism or set of mechanisms that drives relative motion of one or more portions of the instrument relative to one another and/or relative to the cassette (or vice versa). In some cases, the fluidics assembly may be engaged with the cassette manually.

The fluidics assembly may include at least one pressure source 62, such as one or more pumps 64, 66. Each pressure source may be a source of positive pressure and/or negative pressure (i.e., a pressure respectively greater or less than atmospheric pressure). For example, the fluidics assembly may include a vacuum pump 64 configured to be a source of negative pressure applied to the cassette. Alternatively, or in addition, the fluidics assembly may include a positive pressure pump 66 configured to be a source of positive pressure applied to the cassette. In some cases, the same pump (e.g., a reversible pump) may be a source of negative pressure and positive pressure applied to the cassette at different times. In some cases, both negative and positive pressure may be applied to the cassette (and particularly to a chip thereof) at the same time. Exemplary pumps that may be suitable include diaphragm pumps, syringe pumps, rotary pumps, etc.

Fluid may be contained in the fluidics assembly by any suitable fluidic containers 68 such as one or more conduits 70 (e.g., tubing), at least one manifold 72, one or more chambers, or any combination thereof. In any event, the fluidic containers provide a cassette interface structure 74 (such as manifold 72) having one or more ports 76 for fluid communication with the cassette. In other words, pressure originating from the pressure source may be applied to the cassette via ports 76 of interface structure 74.

Flow of fluid through the fluidics assembly may be regulated by one or more valves 78-84. Each valve may be an on/off valve 78, 80, or a valve that is continuously adjustable. In some cases, the valve may be a continuously adjustable valve 82, 84 that is included in a pressure controller 86, 88 that achieves and maintains pressure at a set point. The valve may provide any suitable number of connections to pumps, conduits, ports, and/or vents, such as a two-, three-, or four-way valve, among others.

Pressure in the fluidics assembly may be measured at any suitable positions therein by one or more pressure sensors 90-94. The pressure sensors may include an endpoint pressure sensor 90 configured to detect pressure changes associated with ports 76 and resulting from air intake by channels of cassette 54. The sensors also or alternatively may include pressure sensors 92, 94 incorporated into pressure controllers 86, 88, respectively.

Drive assembly 60 may be configured to drive relative motion, indicated by a double-headed arrow at 100, of manifold 72 (and/or ports 76) and cassette 54 (and/or seat 56). The drive assembly first may bring the manifold (and/or ports) and the cassette together, into sealed engagement with one another, to fluidically connect (i.e., create fluid communication between) the manifold/ports and the cassette, for emulsion formation. Then, the drive assembly may separate the manifold/ports and the cassette from one other, to break the sealed engagement and terminate the fluid communication. In any event, the drive assembly may drive motion of the manifold/ports, the cassette (and/or seat), or a combination thereof, in parallel or serially.

The drive assembly may be equipped with one or more force-generation devices, such as one or more motors 100, 102. Each motor may be a rotary motor or a linear motor, among others. In some cases, motor 100 or another force-generation device may drive horizontal motion (of the manifold/ports and/or cassette/seat), and motor 102 or another force-generation device may drive vertical motion (of the manifold/ports and/or cassette/seat). In some cases, the manifold/ports and/or the cassette/seat are driven only vertically relative to each other.

Each motor may be connected to a respective carriage 104, 106 via a power train that includes one or more linkages 108, 109, which may include one or more racks, gears, pulleys, cables, lead screws, and/or the like. Each carriage may carry and/or support any suitable combination of components of fluidics assembly 58 and/or a door of the instrument (see below). For example, one or more carriages may carry manifold 72/ports 76, and/or one or more carriages may carry cassette 54 (and seat 56). In some cases, both carriages may carry manifold 72/ports 76 or both may carry cassette 54 (and seat 56). In other examples, one carriage may carry manifold 72/ports 76 and another carriage may carry cassette 54 (and seat 56).

Drive assembly 60 also may be equipped with one or more sensors 110, which may, for example, be position sensors, such as rotary or linear encoders. The position sensors may measure the position and/or velocity of one or more drive assembly components, such as the motors and/or the carriages, among others.

Instrument 52 may incorporate any number of additional sensors, such as cassette sensors 114, 116 and/or an endpoint sensor 117. Each of sensors 114, 116, 117 may be associated with cassette 54, seat 56, and/or manifold 72/ports 76, among others. Each additional sensor may be an optical sensor, an electrical sensor, or the like. The sensor may detect an aspect of the cassette itself, liquid held by the cassette, and/or fluid in contact with the liquid. For example, each sensor may detect whether or not a component of the cassette is loaded in the instrument, whether or not fluid has been loaded properly in the cassette, whether or not an emulsion has been formed, whether or not liquid has been depleted from a container of the cassette, or the like. Further aspects of endpoint sensors 117 are described below in Section VI.

The instrument may include a processor 120 programmed to control and coordinate operation of other instrument components. The processor may be or include any suitable combination of electronic devices or components that send and receive signals and, optionally, manipulate data, in analog and/or digital form. The processor may be in communication with fluidics assembly 58, drive assembly 60, sensors 114-117, and a user interface 122, among others. Accordingly, the processor may be configured to control any combination of pumps 64, 66, pressure controllers 86, 88, valves 78, 80, motors 100, 102, and the like.

User interface 122 may include any mechanism or set of mechanisms for receiving inputs from a user and/or communicating outputs to the user. The interface may include any suitable input device(s), such as a button, a lever, a knob, a mouse, a joystick, a keypad, a touchscreen, a keyboard, a data port, etc. The interface also or alternatively may include any suitable output device(s), such as one or more status lights, a display or screen, a printer, a data port, and/or the like.

FIG. 1 shows an exemplary embodiment of user interface 122. The user interface may have a single input device, namely, a button 124 provided on an exterior of the instrument, in this case, on a door 126. Button 124 (or another user control) may be connected to a switch 128 operated by pressing the button. Pressing the button when the door is closed, as in FIG. 1, may signal the processor to open (and/or unlock) the door via the drive assembly. Pressing the button when the door is open, as in FIG. 2, may signal the processor to close (and, optionally, lock) the door via the drive assembly. In some cases, the processor may proceed, without further user input or participation, to initiate and control a sequence of operations by the drive assembly and fluidics assembly that cause emulsion formation and, optionally, emulsion concentration, in the cassette.

The user interface of instrument 52 also may include one or more indicator lights 130-136 that may communicate a status of the instrument to the user. For example, indicator light 130 may be visible through button 124. Other indicator lights 132-136 may be supported by a body or housing 138 of the instrument. The indicator lights may communicate a status such as (a) emulsion formation in progress, (b) cassette not seated in instrument, (c) cassette is seated, (d) gasket missing, (e) door is locked, or the like.

FIGS. 1 and 2 respectively show instrument 52 in a closed configuration and an open configuration. Housing 138 and door 126 collectively may form a chamber 140 in which seat 56 may be disposed. The position of door 126 may determine the closed or open configuration of the instrument. For example, here, door 126 retracts into chamber 140 to permit access to seat 56. In other words, the door may move translationally when the instrument opens to decrease the size of chamber 140, such that seat 56 is disposed outside rather than inside the chamber. Door 126 may function as a barrier that protects internal components of the instrument. In this way, electronic, fluidic, and mechanical components of instrument 52 (e.g., fluidics assembly 58, drive assembly 60, processor 120, etc.) can remain substantially inaccessible to the user and protected from cleaning agents, such as bleach, that may be used to minimize the chance of cross-contamination between chips/experiments. In other examples, the door may move pivotally or both pivotally and translationally between open and closed configurations.

II. Exemplary Cassette

Figure 4:
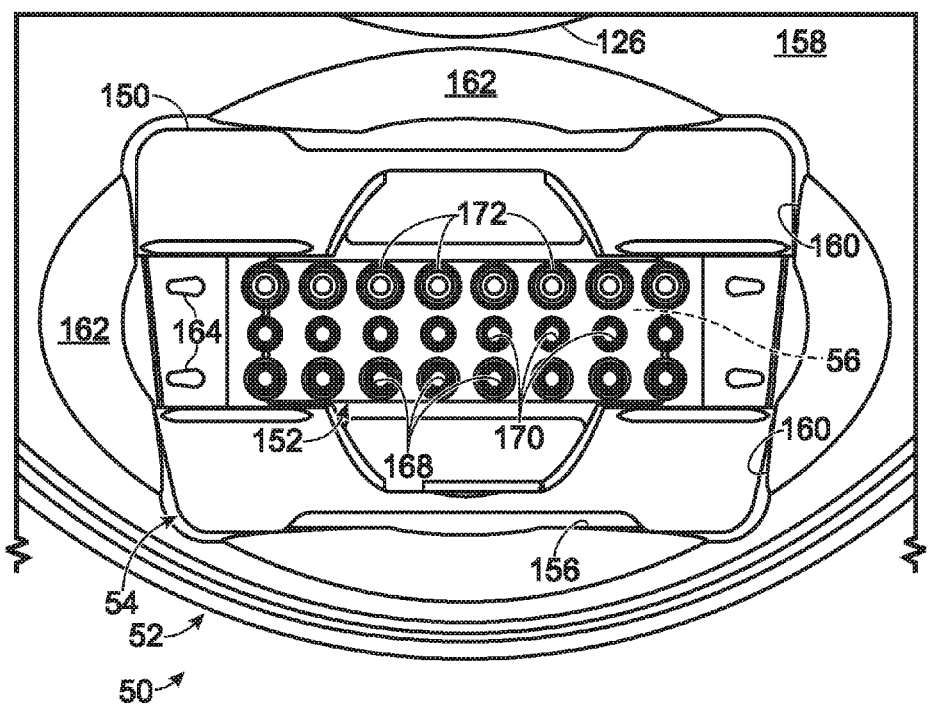
FIG. 4 is a plan view of the cassette and receiving area of FIG. 2, showing a microfluidic chip and a cartridge of the cassette, in accordance with aspects of the present disclosure.
Figure 5:
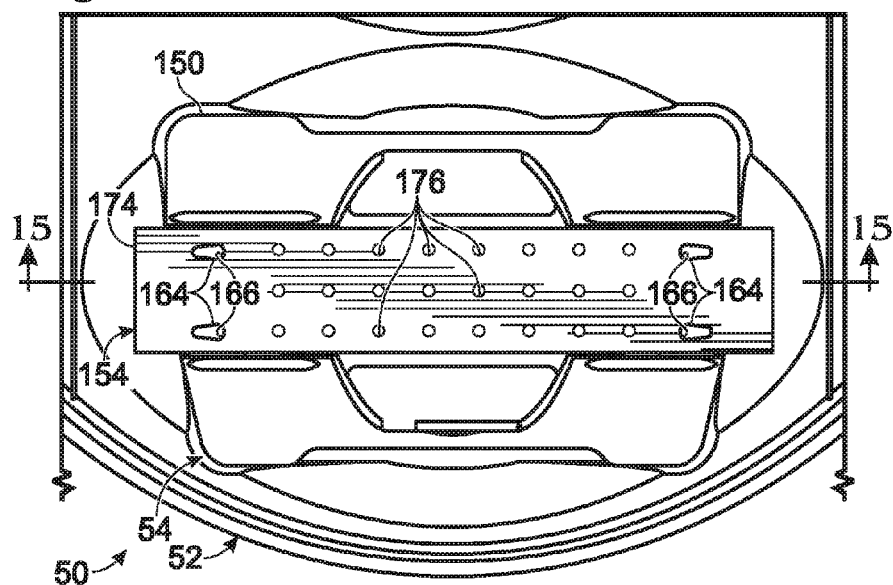
FIG. 5 is a plan view of the cassette and receiving area of FIG. 4 taken with a gasket attached to the cartridge of the cassette and covering wells of the chip.

This section describes exemplary microfluidic cassette 54 that interfaces with instrument 52; see FIGS. 4 and 5.

FIGS. 4 and 5 shows cassette 54 supported by and engaged with seat 56 of instrument 52. The cassette may be any device or assembly configured to be operatively and removably engaged with instrument 52. The cassette may be configured to be readily received by and removed from instrument 52 and is interchangeable with other cassettes. For example, a user may use a set of cassettes each of which can be disposed interchangeably in seat 56, for emulsion formation with the cassettes serially. Cassette 54 may include a cartridge 150, a microfluidic chip 152 (see FIG. 4), and a gasket 154 (see FIG. 5).

Cartridge 150, also termed a chip holder, may be configured to support and position the chip, and in some cases, may lock the chip reversibly to the cartridge. The cartridge may be reusable because the cartridge does not contact any liquid loaded into and driven within microfluidic chip 152. (The instrument may not contact any of the liquid either.)

The cartridge may have any suitable size and shape. For example, the cartridge may have a larger footprint than the chip, such as being wider and/or longer than the chip, to facilitate handling by a user. Also, or in addition, the cartridge may elevate the chip from a bottom surface of the cartridge. The cartridge thus may (or may not) have a greater height than the chip. The cartridge may be shaped to mate with seat 56. For example, seat 56 may be at least generally complementary to the cartridge, such as including an at least generally cartridge-shaped depression 156 formed in a floor 158 of the chamber of the instrument. Depression 156 may have corner wall regions 160 that restrict horizontal motion of the cartridge. Also, the depression may have one or more sloped wall regions 162 that facilitate the ability of the user to grasp the cartridge as the cartridge is being placed manually into the depression and/or removed from the depression. In other examples, seat 56 may project upward from floor 158. In any event, cartridge 150 and seat 56 may be configured such that the cartridge can be installed in only one orientation, to avoid application of pressure by instrument 52 to the wrong parts (e.g., the wrong row of wells) of the microfluidic chip. In the depicted embodiment, cartridge 150 is generally trapezoidal in shape.

Cartridge 150 also may attach gasket 154 to the cassette (see FIGS. 4 and 5). For example, the cartridge may form a plurality of projections, such as hooks 164 or pins, that are configured to be received in apertures 166 of the gasket (see FIG. 5).

Microfluidic chip 152 may form a plurality of wells 168-172 that serve as input containers for prospective emulsion phases and output containers for collected emulsions (see FIG. 4). The chip is described in more detail below in Section III.

FIG. 5 shows gasket 154 attached to cartridge 150. The gasket may be used for emulsion formation only once (i.e., a disposable gasket) or may be used more than once (i.e., a reusable gasket). The gasket may include a substantially planar sheet 174 formed of a conformable and/or resilient material, such as an elastomer (e.g., silicone rubber). The sheet may be sized to cover at least a portion of the chip, such as to at least partially cover any suitable number of the wells of the chip. At least partially covering the wells may limit inadvertent introduction of contaminants into the wells and/or cross-contamination between wells.

The sheet may define apertures 166 at opposing ends and/or sides of the sheet, and an array of orifices 176 (interchangeably termed through-holes) that are arranged in correspondence with wells 168, wells 170, and/or wells 172 of chip 152 (also see FIG. 4). For example, orifices 176 may have the same spacing as the wells and may be alignable (e.g., coaxially) with any number of the wells, such that each of wells 168, each of wells 170, and/or each of wells 172 is overlapped by a different orifice. Each orifice may (or may not) be smaller in diameter than the (inner) diameter of an overlapped well. Accordingly, each orifice may overlap only one well or may be large enough to overlap two or more wells (e.g., overlapping a row or column of wells, among others). The orifice may function as a vent during emulsion formation and/or emulsion concentration and/or may provide fluid communication between ports of the instrument and wells of the chip. When the gasket is operatively disposed on and engaged with the chip, the gasket may be configured to form a circumferential seal with any of the wells of the chip, such as each of wells 168, 170, and/or 172. Exemplary sizes for orifices 176 include a diameter of about 0.2, 0.5, 1, 2, 3, or 5 mm, among others, or less than about one-half of the outer or inner diameter of each corresponding well.

The gasket may be a separate piece from the chip or may be integral to the chip. If integral, the gasket may be substantially permanently attached to the containers of the chip, such that the containers and the gasket cannot be separated from each other without damaging the chip (i.e., the chip has a unitary structure that includes a gasket). The gasket may be co-molded with the containers of the chip or may be formed separately and attached permanently to the chip, such as with an adhesive, by bonding, or the like. In some cases, the gasket may be formed as a plurality of spaced annuluses of elastomeric material disposed on and/or permanently attached to the top surface of the desired containers of the chip, such as each of the output wells. Each annulus may be coaxial with a container of the chip.

The gasket may include a thin sheet or layer of filter paper. The filter paper may be disposed on the resilient sheet and/or may be sandwiched between a pair of resilient sheets to encapsulate the filter paper, among others. In any event, the filter paper may overlap/cover each of the orifices of the sheet. The filter paper may have a pore size selected to reduce particulates from being drawn into the manifold and/or entering containers of the chip from the ambient environment and/or the manifold. The filter paper may reduce contamination. The pore size may be selected such that air flow, venting and/or pressure in the chip and instrument are not affected substantially or adversely. The filter paper may be chosen to be hydrophobic or oleo/hydrophilic, to minimize contamination with, and/or passage into the manifold of, hydrophilic/aqueous or oleo/hydrophobic fluids, respectively.

III. Exemplary Microfluidic Chip

This section describes exemplary microfluidic chip 152 that may be utilized in cassette 54 to form and collect one or more emulsions; see FIGS. 6 to 11.

The term "chip" in the present disclosure describes any device for holding and manipulating fluids, such as prospective and actual emulsion phases. The device may not (or may) include electrical and/or electronic structure. The terms "microfluidic chip" and "microfluidic device" are interchangeable. The term "microfluidic" means that the chip/device defines at least one channel with a characteristic dimension (e.g., diameter, width, and/or depth) of less than one millimeter. A microfluidic chip is not limited otherwise in size, shape, or functionality, except when expressly specified.

Figure 6:
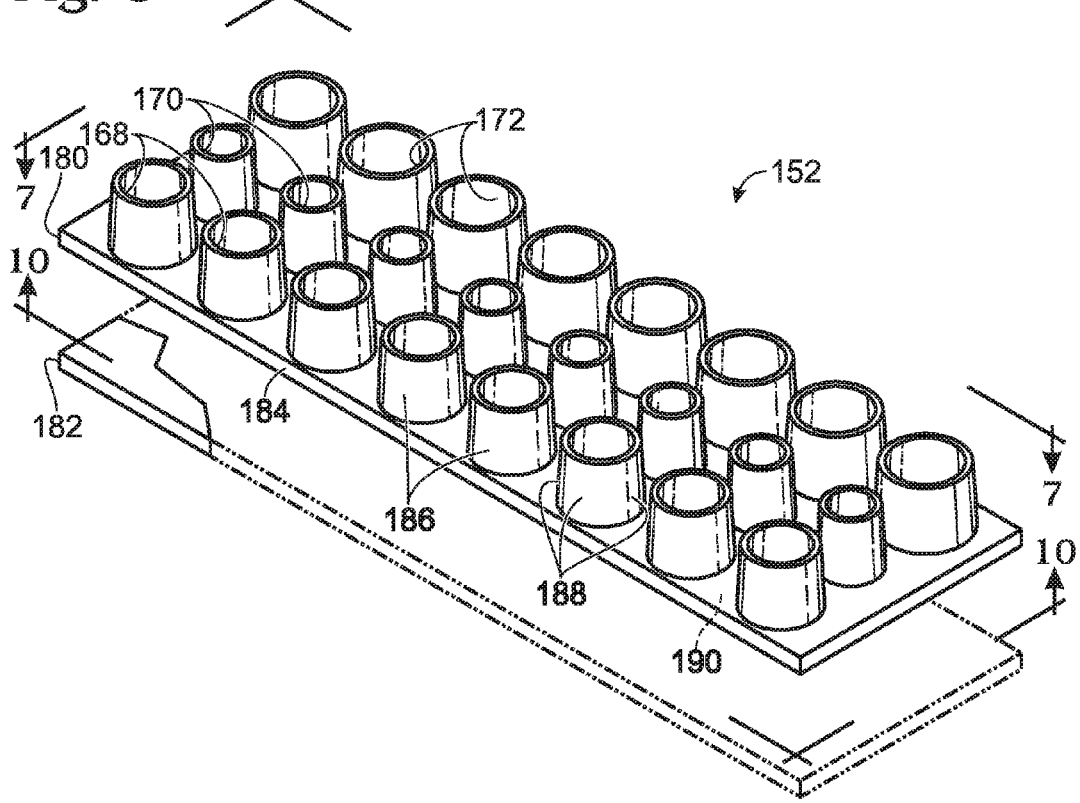
FIG. 6 is an exploded view of the chip of FIG. 4.

FIG. 6 shows an exploded view of chip 152. The chip may be used for emulsion formation only once (i.e., a disposable chip) or may be used more than once (i.e., a reusable chip). The chip may be composed of an upper member 180 and a lower or sealing member 182. The upper and lower members may be substantially irreversibly attached to each other, such as by bonding and/or with an adhesive. In other words, the chip may have a unitary (one-piece) structure, meaning that the chip cannot be separated into two or more pieces without damaging the chip, such as by cutting, breaking, tearing, melting, dissolving, etc. Upper member 180 may form a bottom region or base 184 and a plurality of tubular projections 186 projecting upward from the base. Each tubular projection may form lateral side walls 188 of one of wells 168-170. Lower member 182, which may or may not be a substantially featureless sheet of material or film, may seal a bottom surface 190 of upper member 180. For example, lower member 182 may form a bottom wall of each of wells 168-172 and each channel (see below).

Figure 7:
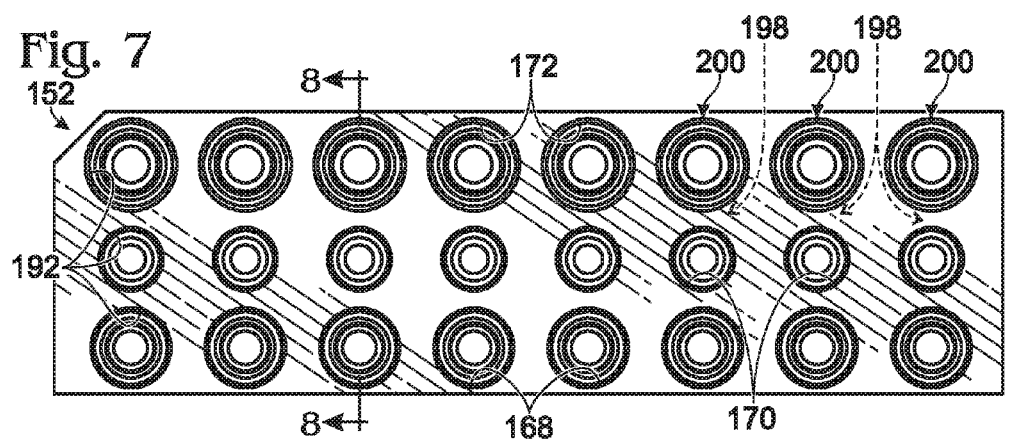
FIG. 7 is a plan view of the chip of FIG. 6, taken generally along line 7-7 of FIG. 6.
Figure 8:
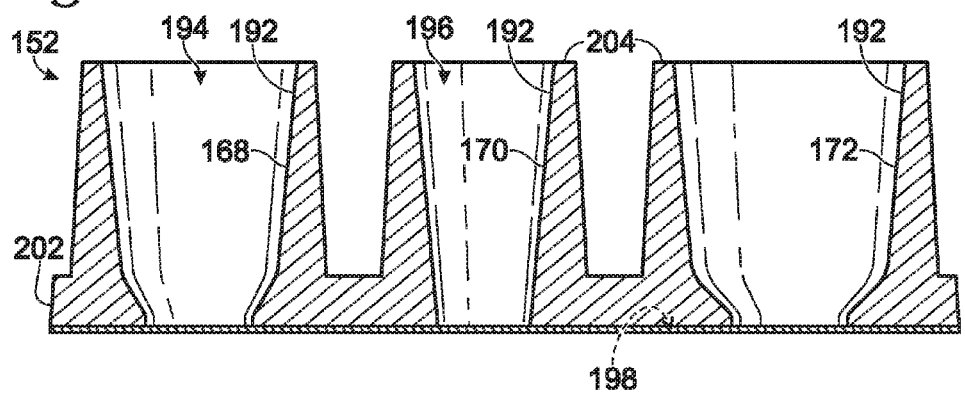
FIG. 8 is a sectional view of the chip of FIG. 6, taken generally along line 8-8 of FIG. 7.

FIGS. 7 and 8 show respective plan and sectional views of chip 152. The chip may provide a plurality of containers 192, such as chambers, wells 168-172, or the like, for holding emulsion phases. A subset of the containers, such as input wells 168, 170 (also termed inlet wells), may provide input reservoirs 194, 196 to receive and hold prospective emulsion phases, and to supply the emulsion phases to one or more droplet generators 198 of the chip. Another subset of containers 192, such as output wells 172 (also termed outlet wells), may provide output containers to receive and collect one or more emulsions from droplet generators 198.

Chip 152 may provide one or a plurality of emulsion formation units 200 each including a droplet generator 198 (see FIG. 7). Units 200 may be substantially identical to one another. The emulsion formation units may be in fluid isolation from each other, such that there is no sharing or mixing of emulsion phases among the units, or may share an input reservoir (such as for a continuous phase). In any event, the units may be used to form a corresponding plurality of separate emulsions collected in the output containers (e.g., wells 172).

Containers 190 structured as wells 168-172 may have any suitable arrangement. The wells may be arranged in rows and columns. In some cases, each column (or row) may be part of a different emulsion formation unit 200. The wells may be spaced in correspondence with a standard well-to-well spacing of a microplate, as published by the American National Standards Institute (ANSI) on behalf of the Society for Biomolecular Screening. For example, the wells within each row may have a center-to-center spacing of about 18, 9, 4.5, 2.25, or 1.125 millimeters, among others. The wells of the same emulsion formation unit (e.g., the wells of a column) may or may not have a spacing that corresponds to a standard microplate well spacing.

Wells 168-172 may have any suitable size and shape. For example, each of the wells in a row may be substantially identical to each other, having the same size, shape, and volume. Wells of different rows and/or within the same column may have different sizes, shapes, and/or volumes. The wells may be configured to form a seal when juxtaposed with a suitably formed gasket. In particular, the top surface of each well may be substantially planar. The top surfaces of wells may be coplanar to enable forming a seal with a substantially planar gasket. In the depicted embodiment, wells 172 are largest, wells 168 are intermediate in size, and wells 170 are smallest. Each well may taper toward a base 202 of the chip (see FIG. 8). The wells of a row and/or all of the wells may have the same height, to form a planar top surface 204 of the chip. The top surface may be engaged with gasket 154 (e.g., see FIG. 5).

Figure 9:
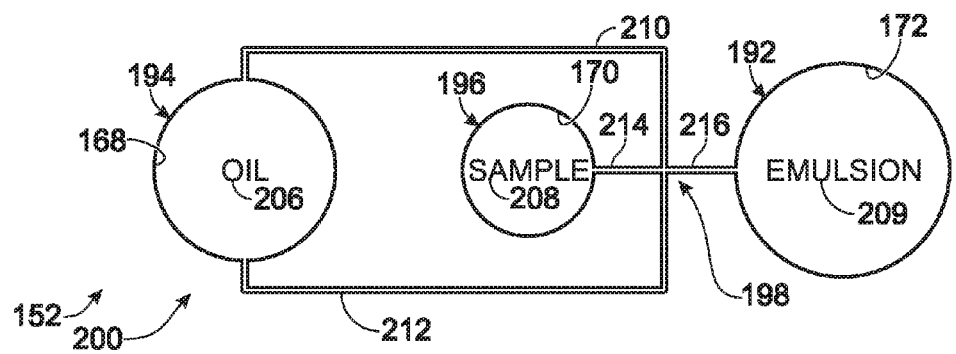
FIG. 9 is a somewhat schematic bottom view of a single emulsion formation unit of the chip of FIG. 6, in accordance with aspects of the present disclosure.

FIG. 9 shows a somewhat schematic bottom view of a single emulsion formation unit 200 of chip 152. Input reservoirs 194, 196 (i.e., wells 168, 170) may hold and supply prospective emulsion phases, such as an oil phase 206 and an aqueous sample 208. Collection container 192 (i.e., well 172) may receive and collect an emulsion 209 formed by droplet generator 198 from oil phase 206 and sample 208. The reservoirs and the collection container may be fluidically interconnected via channels 210-216 that intersect at droplet generator 198. The channels may include one or a pair of oil inlet channels 210, 212, a sample inlet channel 214, and an emulsion outlet channel 216. In some embodiments, each of oil inlet channels 210, 212 may extend from a different input reservoir. In some embodiments, the emulsion formation unit may include only one oil inlet channel. Exemplary emulsion phases and other exemplary configurations for droplet generators, channels, input reservoirs, and collection containers, among others, that may be suitable for chip 152 are described in the patent documents listed above under Cross-References, which are incorporated herein by reference, particularly U.S. Patent Application Publication No. 2010/0173394 A1, published Jul. 8, 2010; U.S. Patent Application Publication No. 2011/0217712 A1, published Sep. 8, 2011; and PCT Patent Application No. WO 2011/120024, published Sep. 29, 2011.

Figure 10:
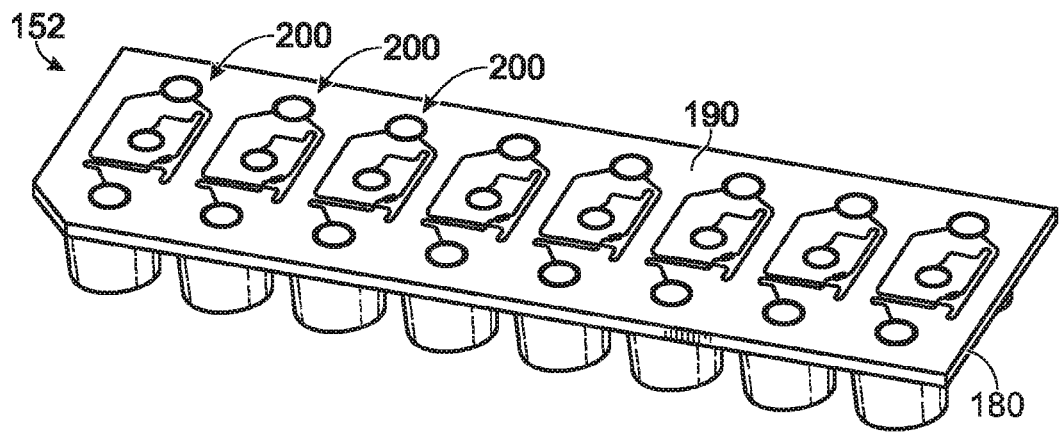
FIG. 10 is a bottom view of an upper member of the chip of FIG. 6, taken generally along line 10-10 of FIG. 6.
Figure 11:
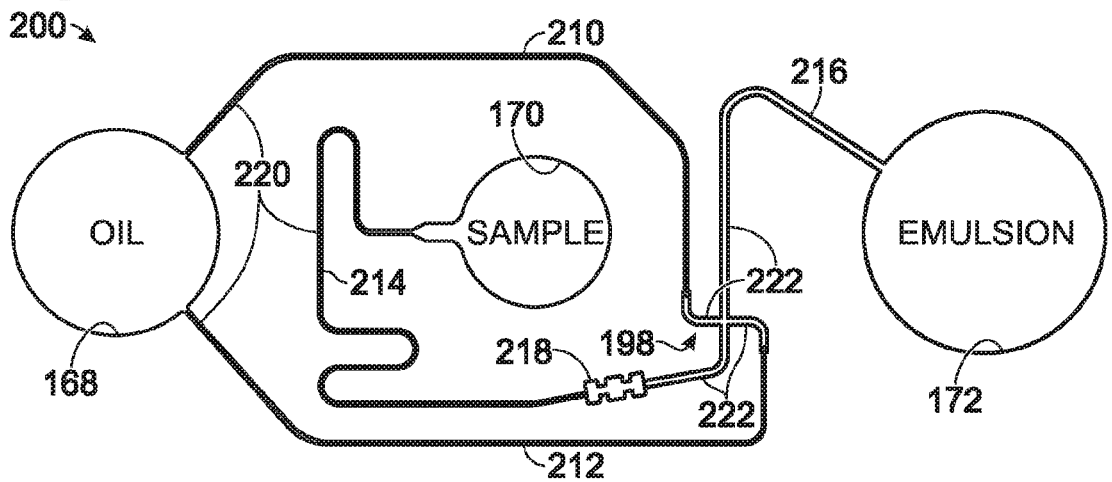
FIG. 11 is a less schematic bottom view of the single emulsion formation unit of FIG. 9.

FIGS. 10 and 11 show less schematic, bottom views of emulsion formation units 200 (FIG. 10) or one of the units (FIG. 11) of chip 152 in the absence of lower member 182 (also see FIG. 6). Channels 210-216 and droplet generator 198 of each unit 200 may be formed predominantly in bottom surface 190 of upper member 180, with only a bottom wall of each channel and droplet generator formed by lower member 182. In other embodiments, at least a portion of one or more of the channels and/or the droplet generator of each unit 200 may be formed in the top surface of lower member 182.

Channels 210-216 may have different cross-sectional sizes (i.e., diameters/widths and/or depths) and/or lengths and/or may vary in size along each channel. The cross-sectional size(s) and the lengths may be selected to provide a desired resistance to flow and thus a desired ratio of emulsion phases flowing through droplet generator 198, to form droplets of the desired size, to enhance droplet stabilization after droplet formation, to form at least one air trap 218 in an inlet channel (e.g., sample inlet channel 214), or any combination thereof, among others.

In exemplary embodiments, channels 210-216 form a channel network that interconnects the wells of an emulsion formation unit. The channel network may have a narrower/shallower region 220 for greater flow resistance, and a wider/deeper region 222 downstream of region 220 for droplet formation and stabilization. In other words, the cross-sectional size of the channel network may increase toward the collection container of the unit. Region 222 may begin upstream of droplet generator 198 for each of the inlet channels and may extend from the droplet generator via outlet channel 216. Each channel may taper in a direction parallel to the depth axis of the channel. For example, each channel may taper toward the top (or the bottom) of the chip. In some cases, each channel may have a trapezoidal cross-sectional shape and/or may have a depth and a width that are about the same. In exemplary embodiments, intended only for illustration, channel portions of region 220 may have a depth and a width of about 50-100, or 60-80 micrometers, among others, channel portions of region 222 may have a width and a depth of about 80-150 or 90-120 micrometers, among others, and the droplets generated may have a volume of about 0.1-10 nanoliters, among others. Further aspects of channel shapes and sizes that may be suitable for the chip are described in the patent documents listed above under Cross-References, which are incorporated herein by reference, particularly PCT Patent Application No. WO 2011/120024, published Sep. 29, 2011.

IV. Exemplary Cartridge

Figure 12:
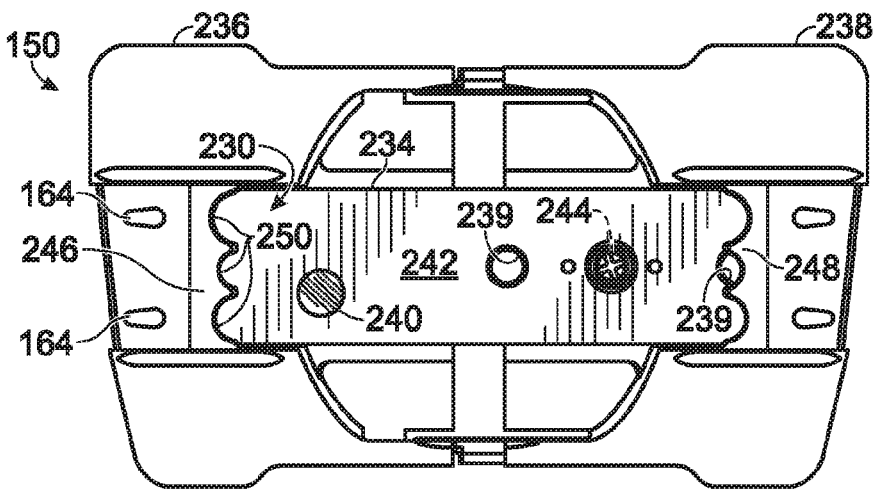
FIG. 12 is a plan view of the cartridge of FIG. 4 taken with the cartridge in an open configuration that permits the chip to be loaded into and removed from the cartridge, in accordance with aspects of the present disclosure.
Figure 13:
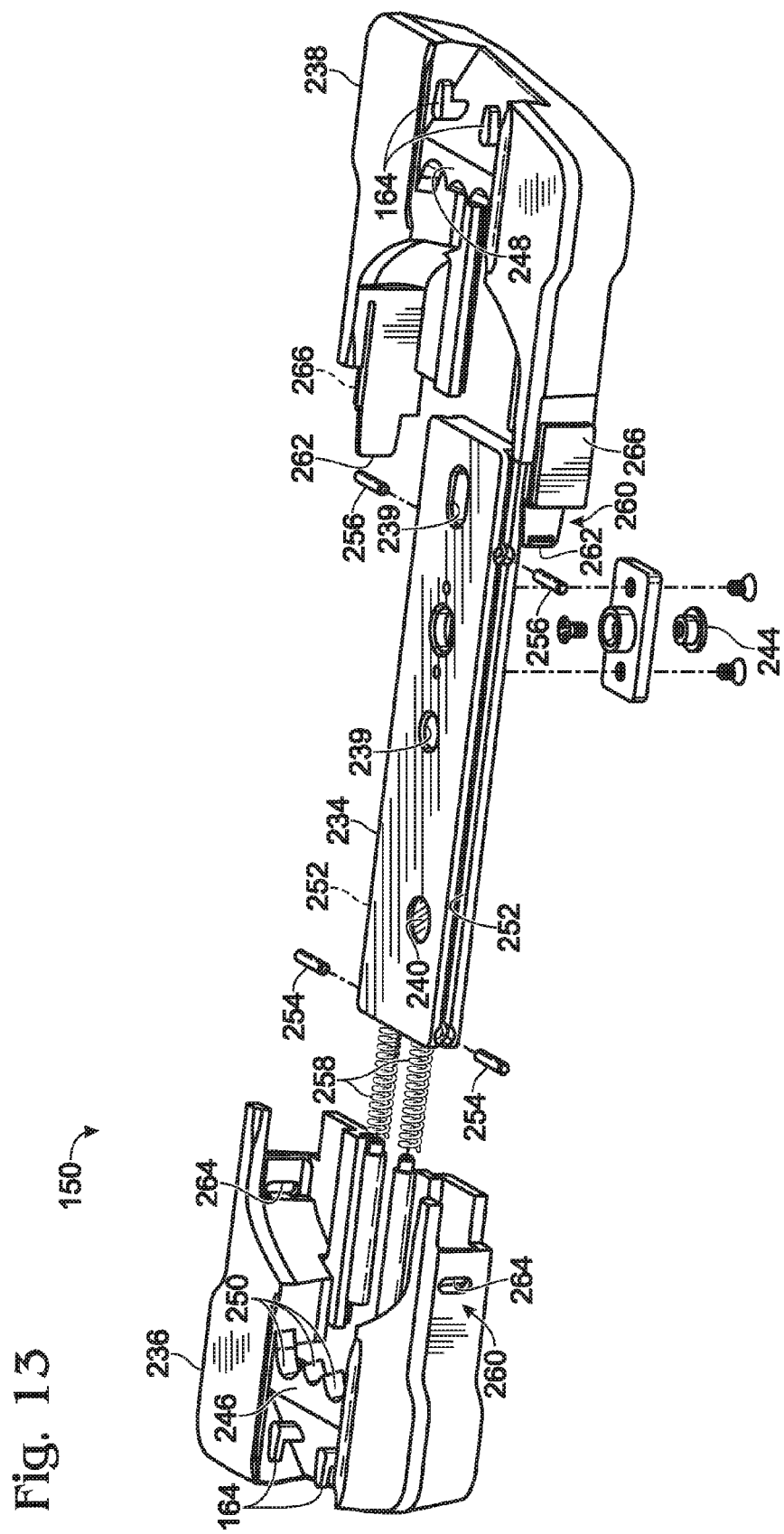
FIG. 13 is an exploded view of the cartridge of FIG. 12, taken generally from above and to the side of the cartridge.

This section describes exemplary cartridge 150 of cassette 54 for holding the microfluidic chip and the gasket; see FIGS. 12 and 13. Additional aspects of the cartridge are described above in Section II (e.g., see FIGS. 4 and 5).

FIG. 12 shows cartridge 150 in an open or receiving configuration (compare with FIG. 4). The open cartridge forms a receiving area 230 sized to receive chip 152 from above the cartridge. The receiving area may include a beam or central portion 234 that supports the chip and a pair of retainers 236, 238 with an adjustable spacing. Beam 234 (and/or the retainers) may define one or more openings 239 for mating with seat 56 of instrument 52 (see Section V). The beam can be constructed to ensure level presentation of the chip to the manifold for making a solid, uniform seal across all containers in contact with manifold. An exemplary material for the beam is stainless steel.

The cartridge may be equipped with an optical element 240, which may be reflective or otherwise detectable optically. The optical element may be on a surface of the cartridge, such as an upwardly, downwardly, or laterally facing surface. In exemplary embodiments, the optical element is disposed on a floor 242 of the receiving area.

The cartridge also or alternatively may be equipped with a contact element 244 (also see FIG. 13), which may be electrically conductive. In exemplary embodiments, conductive element 244 is disposed on an underside of the cartridge, such as on a bottom surface of beam 234 (and/or one of retainers 236, 238). The conductive element may be used to detect that the cartridge is seated in place within the receiving area.

Retainers 236, 238 may form retaining structure for chip 152 and gasket 154. For example, each retainer may provide an undercut wall 246, 248 capable of projecting over and overlapping a region of base 202 of chip 152 (e.g., also see FIGS. 7 and 8). Each wall 246, 248 may define notches 250 capable of receiving a column of wells 168-172 disposed near an end of the chip. Also, each retainer may provide one or more projections, such as hooks 164 or pins, to receive the gasket.

FIG. 13 shows an exploded view of cartridge 150. Beam 234 may form lateral tracks 252 that allow the beam to be slidably mated with each retainer 236, 238. Spring-loaded pins 254, 256 may restrict separation of the beam from the retainers after they have been mated. Retainers 236, 238 may be biased toward the open configuration of FIG. 12 by one or more biasing elements, such as springs 258 that urge the retainers apart. The retainers may be urged together and fastened to each other in a closed configuration with a fastening mechanism 260 formed on one or both sides of the retainers. For example, the fastening mechanism may include a tab 262 of one retainer received in a slot 264 of the other retainer. The fastening mechanism on each side may be released by pressing a respective button 266 operatively coupled to tab 262. In some embodiments, the cartridge may be opened by squeezing the cartridge at the buttons. The button(s) can be placed centrally or off-center, among others.

In some embodiments, the cartridge may include hinged clamps that fasten the chip to the support beam at the ends (or sides) of the cartridge, with retainer walls along the top and bottom sides, that is, no buttons or fasteners at the top and bottom. The clamps can be made with features (e.g., notches 250) that match the shapes of the outer surface of the wells on the left and right sides of the chip in the cartridge for additional restriction of motion and clamping efficiency.

V. Exemplary Seated Configuration for a Cassette in the Instrument

Figure 14:
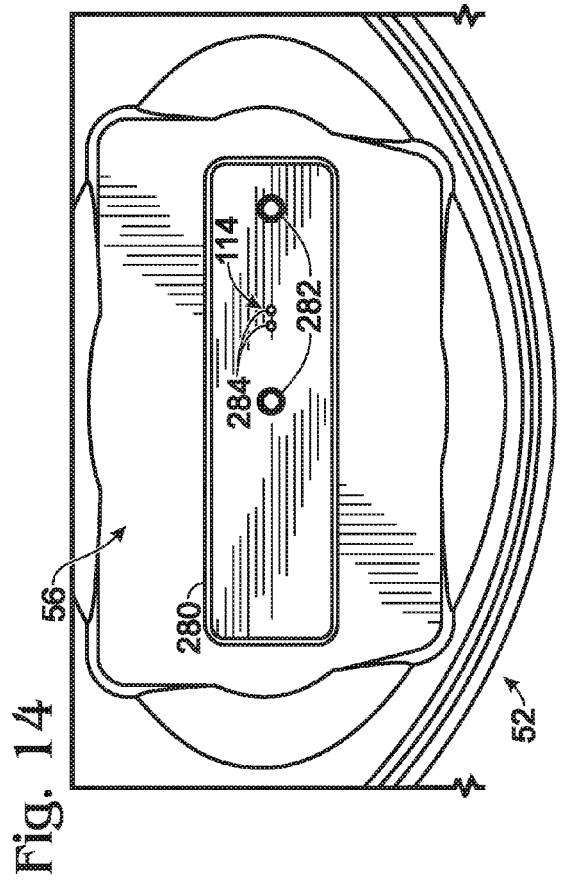
FIG. 14 is a plan view of the receiving area of the instrument of FIG. 2, taken as in FIG. 4 but without the cassette.
Figure 15:
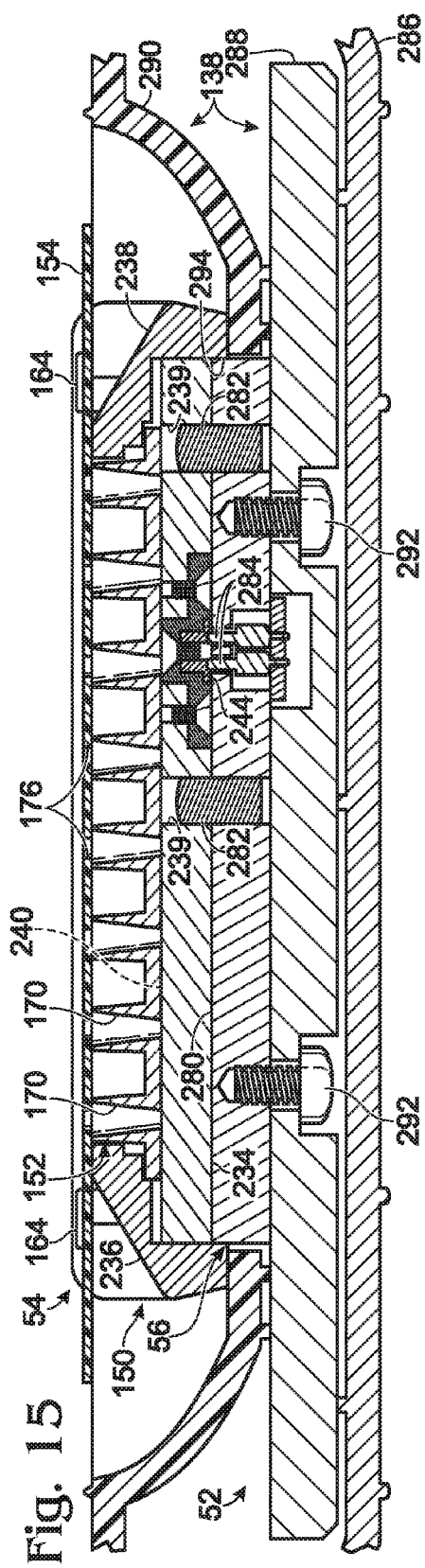
FIG. 15 is a sectional view of the cassette and receiving area of FIGS. 5 and 14, taken generally along line 15-15 of FIG. 5.

This section describes an exemplary seated configuration for the cassette in the instrument, and sensors of the instrument that may detect the seated configuration; see FIGS. 14 and 15.

FIG. 14 shows seat 56 of instrument 52, without cassette 54 (compare with FIG. 4). Seat 56 may include a platform 280 that provides one or more pins 282 for mating with cartridge 150. Platform 280 also may provide electrodes 284 of cassette sensor 114 (also see FIG. 3) to detect contact of seat 56 with the cartridge.

FIG. 15 shows a sectional view of cassette 54 and seat 56 taken with the cassette operatively disposed in instrument 52. Housing 138 of the instrument may include an exterior housing portion 286, a base plate 288, and an interior housing portion 290. The interior housing portion may at least partially define chamber 140 of the instrument (e.g., see FIGS. 1 and 2) and may form at least a portion of seat 56. Platform 280 may be secured to the housing, such as to base plate 288, with fasteners 292.

Cartridge 150 of the cassette may be mated with platform 280. The cartridge may define a recess 294 that receives a body of the platform, and/or pins 282 of the platform may be received in openings 239 of the cartridge. Contact element 244 may be engaged with electrodes 284, which allows the instrument to detect that the cartridge is properly positioned in the instrument by engagement with seat 56.

Cassette sensor 116 (see FIG. 3) may be positioned adjacent the cassette, such as supported by manifold 72 above the cassette, to detect optical element 240 of the cartridge. Sensor 116 may include a light source to illuminate the optical element with incident light, and a photosensor to detect light reflected by the optical element. Chip 152 may be sufficiently translucent to permit passage of incident and reflected light. In contrast, gasket 154 may be sufficiently opaque to block passage of the incident light, without substantially reflecting the incident light back to the photosensor. Accordingly, through the use of cassette sensors 114, 116, the instrument may determine whether the cartridge is loaded and seated in the instrument, and, if seated, whether the gasket is present.

VI. Exemplary Structure and Operation of a Fluidics Assembly for the INSTRUMENT

This section describes exemplary structure of fluidics assembly 58 of instrument 52 and exemplary operation of the fluidics assembly on cassette 54 to form and concentrate emulsions; see FIGS. 16 to 20.

Figure 16:
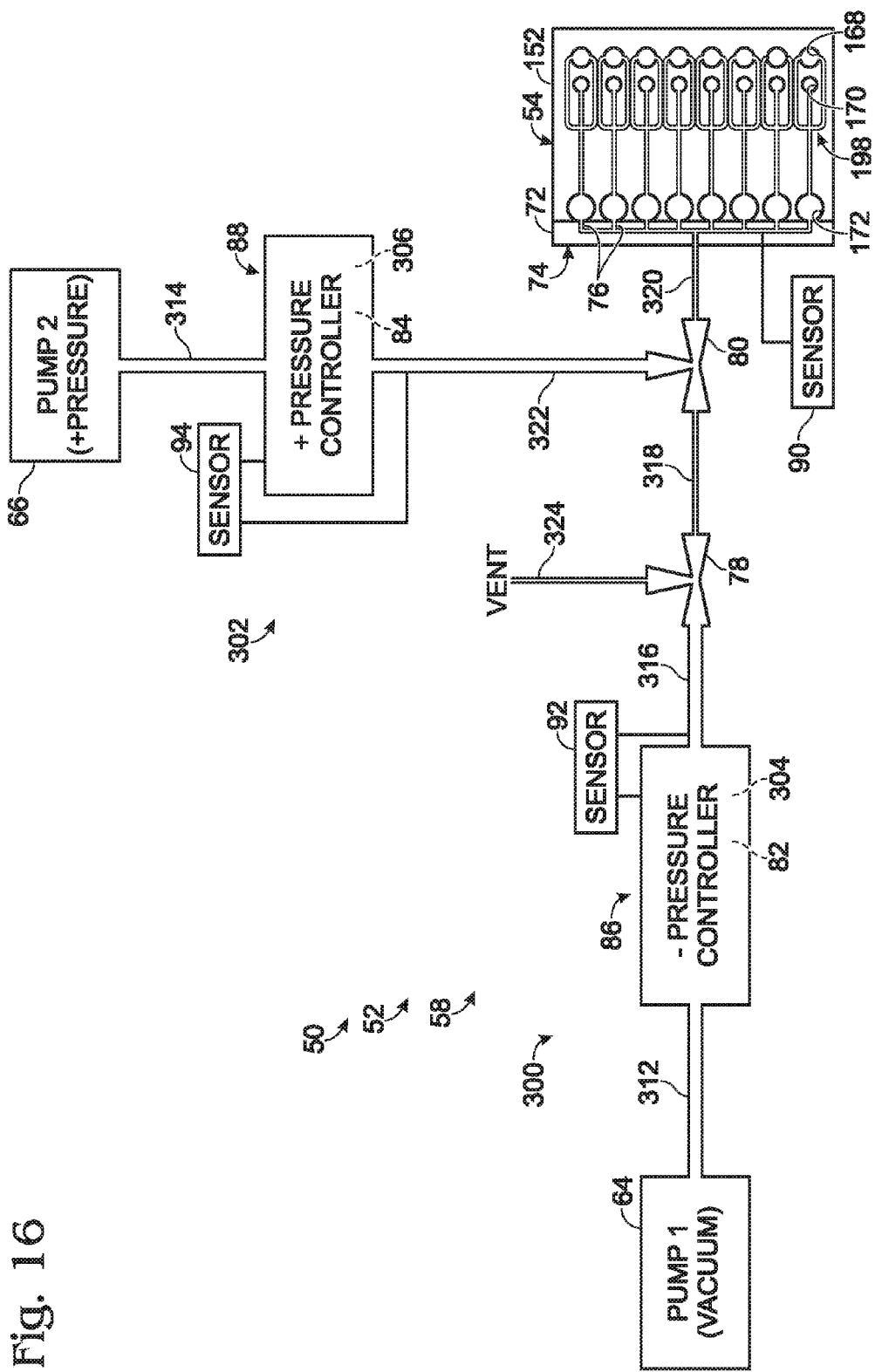
FIG. 16 is a schematic view of the fluidics assembly and chip of the system of FIG. 1, taken with a manifold of the fluidics assembly in fluid communication with the chip.

FIG. 16 shows a schematic view of fluidics assembly 58 operatively interfaced with chip 152 via cassette interface structure 74, namely, manifold 72 with ports 76. Each port may be fluidically connected to one or more wells 172 of chip 152. Pressure may be applied to the chip with a negative pressure portion 300 and a positive pressure portion 302 of the fluidics assembly. For example, negative pressure may be applied first by negative pressure portion 300 to form a set of emulsions that are collected in wells 172. Then, the emulsions may be concentrated with application of positive pressure by positive pressure portion 302. In some cases, positive pressure may be applied to the chip to drive emulsion formation. For example, positive pressure may be applied to input wells 168, 170 to drive droplet generation and emulsion collection. In some cases, both negative pressure and positive pressure may be applied to the chip to drive emulsion formation. For example, negative pressure may be applied to output wells 172 and positive pressure may be applied at the same time to at least a subset of the input wells (such as each of wells 168 or each of wells 170). In this way, a first pressure drop may be formed between the oil input wells and the output wells and a second pressure drop may be formed between the sample input wells and the output wells. The magnitudes of the pressure drops may be set or adjusted to achieve desired relative and/or absolute flow rates for the oil phase and the sample.

Each of pressure portions 300, 302 may include a respective pump 64 or 66 and a respective pressure controller 86 or 88. (In some cases, a pump may be used with two controllers, e.g., with another valve included between the pump and the controllers.) The pump may act as a source of negative or positive pressure for the pressure portion, and the pressure controller may adjust the level of negative or positive pressure in a reservoir or region of the pressure portion, in order to adjust the level of pressure applied to chip 152. However, in some embodiments, the pump may be fluidically isolated from the chip and/or not pumping fluid when the pressure is applied to the chip. In other words, the pump may be used as a source of pressure to establish a positive or negative pressure in a reservoir, and then the established pressure may be applied to the chip from the reservoir without any further participation of the pump.

Each pressure controller may include a respective valve 82 or 84, a respective pressure sensor 92 or 94, and a control device 304 or 306 (e.g., a proportional (P) controller, a (PI) proportional-integral controller, a proportional-integral-derivative (PID) controller, or the like). Each pressure controller may form a feedback loop. The control device may receive a value for a set point pressure and may operate the valve of the controller based on signals received from the sensor to achieve and maintain the set point pressure. The sensor of the pressure controller may detect pressure at a position that is fluidically closer to the chip (or fluidically closer to the pump) than the controller's valve.

Each pressure portion also may include a first pressure reservoir disposed fluidically between the pump and the pressure controller. The first reservoir may be a chamber and/or may be a conduit 312 or 314 that provides fluid communication between a pump and its respective controller. Conduits 312, 314 or other first reservoirs may (or may not) be of substantially larger diameter and/or volume than any combination of conduits 316-322 disposed fluidically closer to the chip. For example, the inner diameter of either or both of conduits 312, 314 or any other first reservoirs may be at least about 2, 5, or 10 times the inner diameter of any of conduits 316-322, and especially conduits 318, 320. Also, or alternatively, the volume of either or both of conduits 312, 314 or any other first reservoirs may be at least about 10, 20, 50, or 100 times the volume of any combination of conduits 316-322, and especially conduits 318, 320.

The pressure portion also or alternatively may include a second pressure reservoir disposed fluidically between the pressure controller and the chip. The second reservoir may be a chamber and/or may be a conduit 316 or 322 that provides fluid communication between a pressure controller and a valve 78 and/or 80 disposed fluidically between the pressure controller and the chip. If both first and second reservoirs are present in a pressure portion, the first reservoir may (or may not) have a substantially larger volume than the second reservoir, such as at least about 2, 5, 10, 20, or 50 times the volume of the second reservoir. In turn, conduits 316, 322 or other second reservoirs may (or may not) be of substantially larger diameter and/or volume than any combination of conduits 318, 320 disposed fluidically closer to the chip. For example, the inner diameter of either or both of conduits 316, 322 or any other second reservoirs may be at least about 2, 5, or 10 times greater than the inner diameter of conduits disposed fluidically closer to the chip, and especially conduits 318, 320. Also, or alternatively, the volume of either or both of conduits 316, 322 or any other second reservoirs may have at least about 10, 20, 50, or 100 times greater than the volume the fluidics assembly disposed fluidically between either conduit and the chip, such as the volume enclosed by conduits 318, 320.

The use of isolatable pressure reservoirs allows a reservoir to be charged with positive or negative pressure from a pump and/or a larger reservoir. The pressure may be stored (e.g., briefly) in the reservoir, in isolation from the pump, the chip, and/or an adjacent reservoir. The stored pressure then may be shared with another reservoir and/or the chip, without substantial diminishment of the magnitude of the stored pressure, if the volume in which the pressure is stored is not increased substantially when the stored pressure is placed in fluid communication with another volume of the pressure portion.

Fluidics assembly 58 may be operated as follows in response to a signal to form emulsions. Vacuum pump 64 may be turned on. Conduit 312 (i.e., a first reservoir) may be charged to a negative pressure, such as about −7 psi (∼−48 kPa (kilopascals)). Pump 64 may (or may not) be turned off. A check valve in or adjacent the pump may prevent loss of negative pressure from the first reservoir through the pump. Negative pressure controller 86 may establish a negative pressure in conduit 316 (i.e., a second reservoir) according to a set point, such as a negative pressure of less than about −10 psi (∼−69 kPa) (e.g., about −0.5 to −4.5 psi (∼−3.4 to −31.5 kPa). One or both of valves 78, 80 may be adjusted to provide fluid communication among conduits 316-320 and manifold 72, such that the negative pressure is applied to wells 172. The negative pressure may be applied with the pump inactivated, that is, with the pump turned off (not pumping fluid) and/or not fluidically connected to the chip. The pressure controller may continue to control the pressure applied to the chip after fluid communication is created with the chip, or the pressure controller also may be shut off and/or fluidically isolated. Endpoint sensor 90 may monitor the pressure applied to the chip by detecting a corresponding pressure in the fluidics assembly, such as in manifold 74 and/or near ports 76, to allow the instrument to determine when to terminate application of negative pressure. The pressure detected by sensor 90 may be equivalent to the applied pressure or may differ from the applied pressure by a pressure differential caused by resistance to fluid flow between the chip and pressure sensor. To stop application of negative pressure, valve 78 may be adjusted to fluidically isolate conduits 318, 320 and ports 76 from conduit 316, while fluidically connecting the conduits and ports to a vent 324.

The detected pressure (e.g., at the manifold) can be used to maintain a predefined pressure range of applied pressure (e.g., +/−0.05, +/−0.075, +/−0.1, +/−0.25, +/−0.5 psi, etc.). Control of this pressure at the point of emulsion generation may influence the degree of monodispersity of the formed emulsion. Tighter control of pressure may give higher monodispersity (more uniform emulsion droplet size).

Positive pressure pump 66 then may be turned on, and conduit 314 (i.e., a first reservoir) may be charged to a positive pressure, such as about 5-8 psi (∼34 to 55 kPa). Pump 66 may (or may not) be turned off. A check valve in or adjacent the pump may prevent loss of positive pressure from the first reservoir through the pump. Positive pressure controller 88 may establish a positive pressure downstream in conduit 322 (i.e., a second reservoir) according to a set point, such as a positive pressure of less than about 10 psi (∼69 kPa) (e.g., about 0.5 to 10 psi (∼3.4 to 69 kPa)). Valve 80 (and/or valve 78) may be adjusted to provide fluid communication among conduits 320, 322 and manifold 72, such that the positive pressure is applied to wells 172. The positive pressure may be applied with the pump inactivated, that is, with the pump off and/or not fluidically connected to the chip. The pressure controller may continue to control the pressure applied to the chip after fluid communication is created with the chip or the pressure controller also may be shut off. To stop application of positive pressure, valve 80 may be adjusted to fluidically isolate conduit 320 and ports 76 from conduit 322, while fluidically connecting conduit 320 and the ports to vent 324.

The conduits flanking the pressure controllers (e.g., conduits 312, 314, 316 and/or 322) may function as reservoirs, as described above. Each reservoir may have a volume that is substantially greater than the volume of conduits 318 and/or 320 and the channels of the manifold, such that the reservoir can apply pressure to the chip after inactivation of the pump, that is, when the pump is isolated from downstream conduits and/or turned off. By applying pressure to the chip with a stored negative and/or positive pressure (e.g., stored as a gas volume with a positive or negative pressure in conduits 312 and/or 316 and 314 and/or 322), instead of by active pumping, a more uniform and reproducible pressure can be applied, which may produce better emulsion formation.

Figure 17:
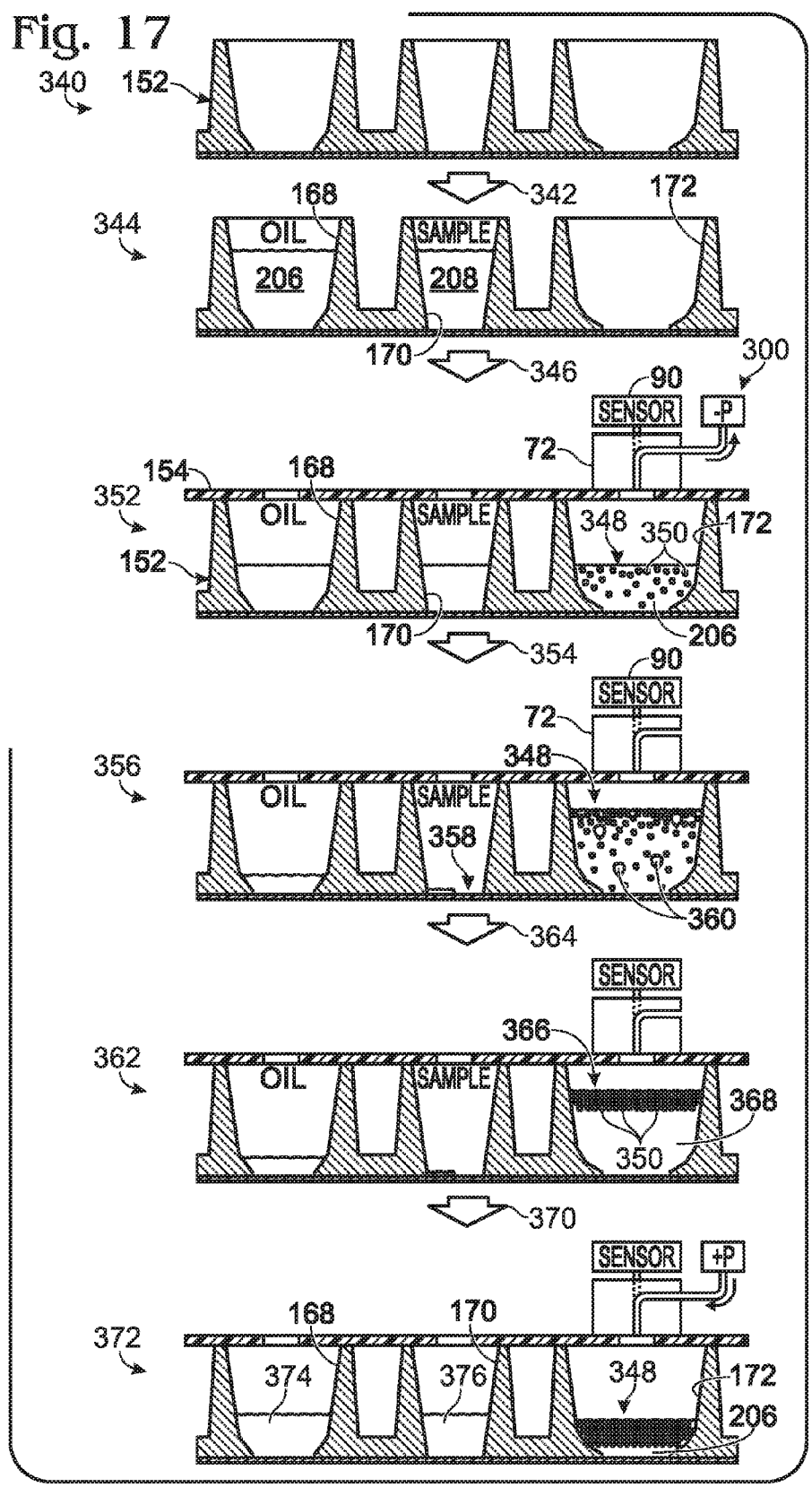
FIG. 17 is a somewhat schematic flowchart illustrating exemplary formation and concentration of an emulsion with the system of FIG. 1, in accordance with aspects of the present disclosure.

FIG. 17 shows a flowchart illustrating exemplary formation and concentration of an emulsion with emulsion formation system 50. The procedures illustrated in the flowchart may be performed in any suitable order and combination.

Microfluidic chip 152 may be selected, indicated by 340. The chip may be assembled with cartridge 150, and optionally locked to the cartridge.

Prospective emulsion phases 206, 208 may be dispensed respectively to wells 168 and wells 170 of the chip, indicated by an arrow at 342, to produce a phase-loaded configuration 344 of the chip. The same prospective emulsion phase 206 (e.g., a prospective continuous phase, such as an oil phase including surfactant(s)) may be dispensed to each of wells 168 of the chip and the same or different prospective phases 208 (e.g., prospective dispersed phases, such as different aqueous samples) may be dispensed to each of wells 170 of the chip. In some embodiments, the aqueous samples may contain salts, surfactant(s), and biological components, such as enzymes, proteins, dNTPs, and/or other polymerase chain reaction constituents, among others. Dispensing phases into each of wells 168 and/or into each of wells 170 may be performed in parallel (such as with a multi-channel pipette) or in series. In some cases, at least about twice the volume of oil phase 206 relative to sample phase 208 may be disposed in the wells. In exemplary embodiments, intended for illustration only, about 10-200 microliters of oil phase 206 may be disposed in each of wells 168 and about 5-100 microliters of sample phase 208 in each of wells 170. In any event, wells 172 may (or may not) be empty at this point. Further aspects of prospective emulsion phases that may be suitable for forming emulsions are described in the patent documents listed above under Cross-References, which are incorporated herein by reference, particularly, U.S. Patent Application Publication No. 2011/0217712 A1, published Sep. 8, 2011

Negative pressure ("−P") may be applied to the chip at wells 172, indicated by an arrow at 346. Gasket 154 may be disposed on the chip, manifold 72 engaged with the gasket, and negative pressure applied to chip 152 at wells 172 via negative pressure portion 300 of the fluidics assembly of the instrument. An emulsion 348 of droplets 350, composed of phase 208 and disposed in continuous phase 206, may be created at each droplet generator and collected in each well 172, to produce a phase-processing configuration 352, during which all of wells 168, 170 still contain sufficient fluid for further emulsion formation. Droplets 350 may be buoyant (or may sink) in the continuous phase and thus may float upward (or sink downward) and accumulate in an upper (or lower) region of the emulsion. In other examples, positive pressure applied to wells 168, 170 may drive emulsion formation.

Endpoint sensor 90 may monitor a pressure of negative pressure portion 300 as emulsion formation is occurring, such as in configuration 352. Use of an endpoint sensor enables a majority (greater than one-half) of each sample to be converted to an emulsion. Sensor 90 generally monitors a pressure in or near the manifold, to detect a change in the pressure indicating depletion of liquid (phase 206 and/or 208) from one or more of wells 168, 170 (i.e., one of the input wells is empty). The change may meet a predefined condition corresponding to a pressure change indicative of air intake from a well (168 or 170), into one or more channels, through a droplet generator, into and/or through an output well (172), into the manifold, or any combination thereof. For example, the change may be a drop in the level of vacuum that occurs for at least a predefined amount of time, to at least a predefined level, at at least a predefined rate or acceleration, any combination thereof, or the like. In some cases, the pressure sensor can detect the pressure change indicative of air intake if only one of the inlet wells 168, 170 is empty. Generally, the wells are loaded such that the sample wells empty first, so, everything else being equal, a sample well loaded with the smallest volume of sample may determine when the endpoint of droplet generation occurs.

In some embodiments, an alternative or additional endpoint sensor 117 may be included in the instrument or cassette (see FIG. 3). The endpoint sensor may detect and/or monitor an aspect of fluid (liquid and/or gas) in the chip and/or of fluid in contact with fluid in the chip. In some cases, the endpoint sensor may detect an aspect of fluid disposed in one or more containers/wells of the chip, such as sample containers/wells of the chip. For example, the endpoint sensor may detect the aspect for at least one or each of the sample containers/wells, at least one or each of the oil containers/wells, at least one or each of the emulsion containers/wells, or any combination thereof.

The endpoint sensor may detect heat capacity of the fluid disposed in one or more containers/wells of the chip. The heat capacity may have a higher value when liquid is present in the containers/well and then may change substantially when the liquid is replaced with air, that is, when a container/well is emptied of its liquid. In some cases, the endpoint sensor may include a plurality of hot wire sensors configured to sense heat capacity of fluid in each of the sample wells, each of the oil wells, and/or each of the output wells of the chip.

The endpoint sensor may be an optical sensor that detects an optical characteristic that changes as the endpoint is reached. For example, the optical sensor may detect refractive index, fluorescence (e.g., if a fluorophore is present in and/or is added to at least one of the prospective emulsion phases), absorbance, scattering, reflectance, or the like, of fluid (liquid and/or gas) in one or more input (and/or output) containers/wells of the chip. As the fluid changes in the container/well (e.g., liquid exits and gas enters, or vice versa), the optical characteristic changes, until a change that meets a predefined condition has occurred (e.g., the refractive index changes when air replaces liquid in an input container/well, the fluorescence intensity decreases to a predefined level when a fluorophore in a prospective emulsion phase is emptied from an input well (or accumulates in an output well), or the like). In some cases, the endpoint sensor may include an optical detector configured to monitor an optical characteristic for each sample well, each oil well, and/or each output well of the chip, to detect a change in one or more of the wells that meets a predefined condition.

In any event, detection of the change causes the instrument to terminate application of negative pressure to wells 172, indicated by an arrow at 354 and illustrated in configuration 356. An empty well 170 is indicated at 358, and air bubbles 360 traveling upward through emulsion 348 are illustrated.

Application of pressure may be stopped at any suitable endpoint. In some cases, the application of pressure may be stopped when greater than 50%, or at least about 60%, 70%, 80% or 90%, on average, of each sample has been converted to droplets. In some cases, the application of pressure may be stopped after air has followed liquid into at least one channel, channel network, and/or droplet generator of the chip, but before the air has followed liquid into all of the output containers (e.g., each of wells 172) of the chip.

In some cases, the instrument may stop applying pressure to the chip during emulsion formation if the detected pressure is not within a predefined range of the set point pressure. This may provide an important control process that is useful when monodisperse droplets are needed.

After stopping emulsion formation, collected emulsion 348 may be left in a resting or packing configuration 362 at atmospheric pressure, indicated by an arrow at 364. During this waiting period, droplets 350 may be permitted to pack themselves together more closely at the top of the emulsion, to produce a close-packed arrangement 366 of droplets. The droplets may be permitted to float upward and pack together more tightly for any suitable time period, such as at least about 1, 5, 10, 30, or 60 seconds, among others. A lower, substantially droplet-free portion 368 of the continuous phase may be produced in the bottom region of the emulsion. In some cases, the droplets may pack together at the bottom of the container, if the droplets are more dense than the continuous phase.

Positive pressure may be applied to wells 172 (or negative pressure to wells 168, 170), indicated by an arrow at 370 and illustrated in configuration 372. The positive pressure may drive continuous phase 206 selectively, relative to the phase 208 and/or droplets 350, from emulsion 348, in reverse along the flow path between each output well 172 and input wells 168, 170. As a result, removed volumes 374, 376 of phase 206 may be collected in wells 168 and/or 170, and emulsion 348 may become more concentrated (i.e., the volume fraction of droplets in wells 172 may be increased and the volume fraction of the continuous phase may be decreased.) The positive pressure may be applied for a preset length of time. Alternatively, the positive pressure may be applied for a length of time that is determined with an algorithm, based on the length of time that negative pressure was applied to wells 172. For example, the positive pressure may be applied for a length of time that is proportional to the duration of emulsion formation. The pressure that concentrates the emulsion may be constant (i.e., a single pressure) or ramped (i.e., a gradient pressure) in one or more timed steps.

Figure 18:
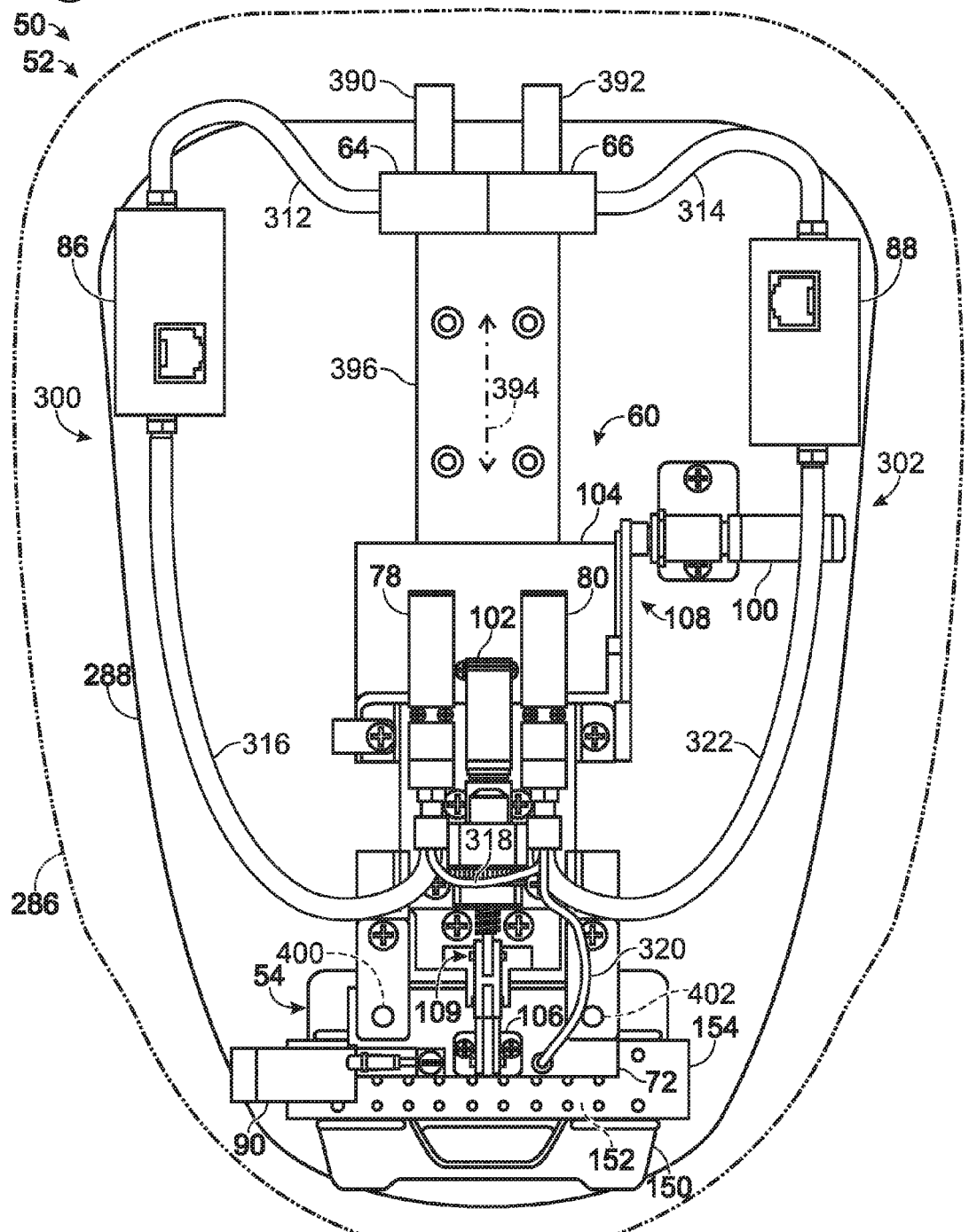
FIG. 18 is a plan view of selected aspects of the system of FIGS. 1 and 5, namely, the fluidics and drive assemblies of the instrument and the cassette seated in the instrument, with the manifold of the fluidics assembly operatively engaged with the cassette.

FIG. 18 shows a plan view of selected aspects of system 50, with cassette 54 seated in instrument 52, and manifold 72 operatively engaged with the cassette. Exterior housing portion 286 is shown in phantom outline. All components are attached to and/or supported by base plate 288.

An exemplary embodiment of fluidics assembly 58 of FIG. 16 is shown in more detail here. The left side of the instrument may provide negative pressure portion 300, and the right side may provide positive pressure portion 302, or vice versa, among others. Pumps 64, 66, may be mounted near the rear of the instrument and each may be connected fluidically to conduit 312 or 314 and to a respective vent 390, 392. The pumps may be mounted with vibration isolation (e.g., via elastomeric grommets). Valves 78, 80 may be mounted to carriage 104 of drive assembly 60, such that the valves can be moved forward and backward in the instrument in response to operation of motor 100. Conduits 316-322 may be connected to valves 78, 80 and pressure controllers 86, 88 in the manner described for FIG. 16.

Drive assembly 60 may use motors 100, 102 respectively to drive forward-and-backward and up-and-down motion of manifold 72. Motor 100 may drive the manifold parallel to a horizontal travel axis 394 defined by a track or guide 396 (e.g., a linear guide). Carriage 104 may be slidably connected to guide 396, for motion along axis 394, and may support valves 78, 80, manifold 72, motor 102, lead screw linkage 109, vertical rails 400, 402, the door of the instrument, endpoint pressure sensor 90, selected electronics, or any combination thereof, among others. Motor 100 may drive carriage 104 via rack-and-pinion linkage 108. Motor 102 may drive manifold 72 vertically along rails 400, 402 via lead screw linkage 109.

Sensors can be used to control horizontal and/or vertical position of the manifold. Sensors, such as optical flags, can be placed to control the position of the horizontal motion. Sensors also can be used to control the z-position or vertical manifold position. The use of these sensors may facilitate aligning the manifold to the chip and/or wells. Failure to do so can result in failure in operation, for example, due to a pressure leak caused by poor alignment between the orifices in the gasket and the ports in the manifold. The vertical sensor can be placed, for example, near one of rails 400, 402.

Figure 19:
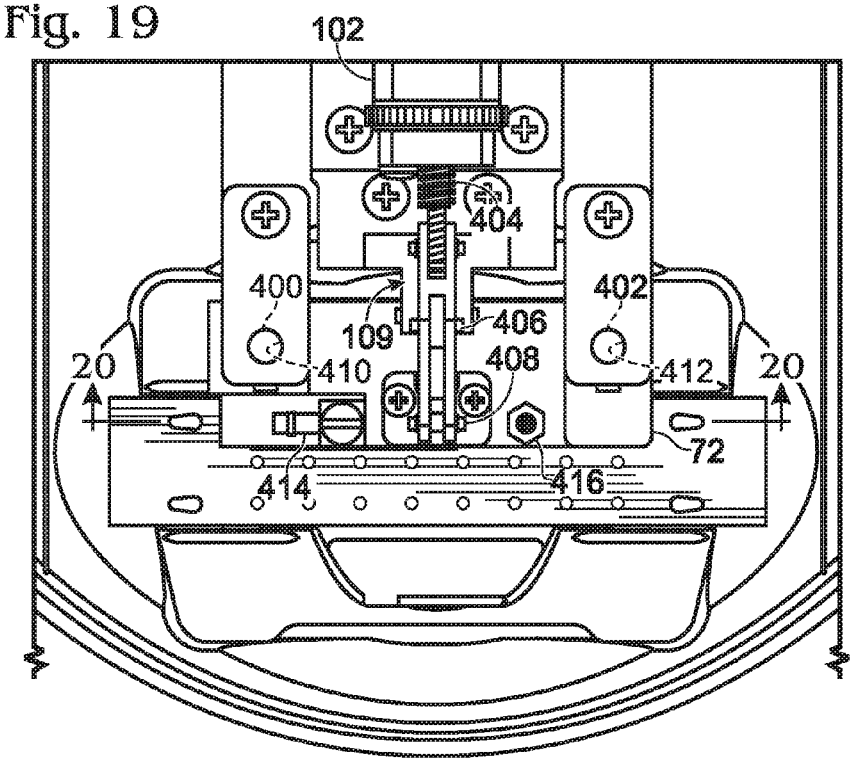
FIG. 19 is a fragmentary plan view of selected aspects of the instrument and cassette of FIG. 18.

FIG. 19 shows further aspects of the vertical drive portion of drive assembly 60. Motor 102 may be operatively connected to a lead screw 404 of linkage 109. Operation of the motor may advance or retract lead screw 404, which respectively lowers or raises manifold 72. Pivot joints 406, 408 of linkage 109 couple net horizontal motion of the screw 404 to vertical motion of the manifold. Rails 400, 402 may be structured as posts received in corresponding bores 410, 412 defined by manifold 72. The manifold may slide along the posts (i.e., vertically) but may be restricted from moving laterally to the posts.

Manifold 72 may form fluidic connections near the top of the manifold. For example, the manifold may be connected fluidically to other parts of fluidics assembly 58 and endpoint sensor 90 by respective couplings 414, 416.

Figure 20:
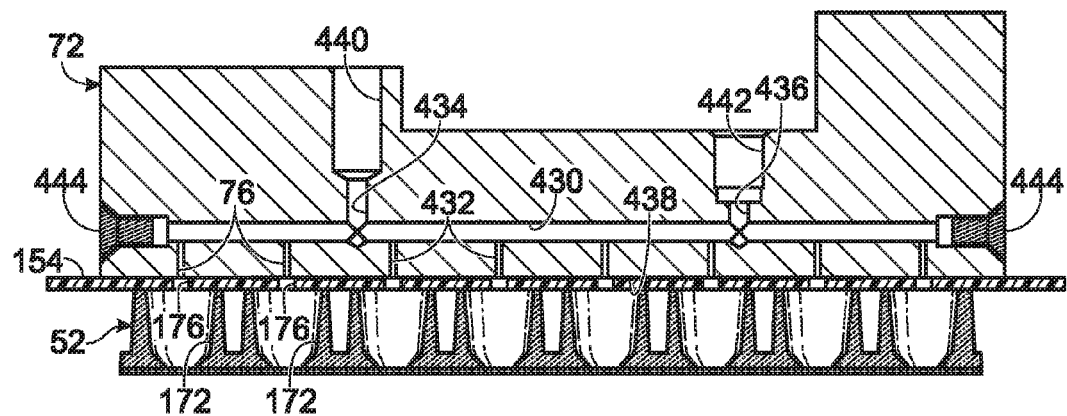
FIG. 20 is a sectional view of the manifold, chip, and gasket of FIG. 19, taken generally along line 20-20 of FIG. 19.

FIG. 20 shows a sectional view of manifold 72, chip 152, and gasket 154 taken through manifold channels 430-436 and ports 76, a row of gasket orifices 176, and wells 172. Main channel 430 of the manifold may have a plurality of branch points forming side channels 432 that extend from the main channel to form ports 76. Each port may extend into the manifold from a lower or bottom surface 438 of the manifold that contacts gasket 154, to form a perimeter seal around each port 76 and orifice 176. The gasket, in turn, seals the perimeter of each well 172. As a result, main channel 430 may be fluidically connected to each well 172.

The manifold may provide any suitable side channels that form ports 76. The manifold may provide the same number of side channels (and ports) as wells 172, for example, eight in the depicted illustration. The side channels may be substantially identical to each other, to provide the same pressure drop through each side channel. In other examples, the manifold may provide the same number of side channels (or ports) as wells 168, 170, with the side channels communicating with the same main channel or respective, fluidically separate main channels. In any event, each side channel may have any suitable diameter. In some examples, the side channel may have a diameter that is substantially less than the diameter of the main channel and/or orifices 176. For example, the side channel may have a diameter that is at least about 2, 3, 4, or 5 times less than that of the main channel and/or the orifices. Each side channel, with a relatively small diameter and sufficient length, may be configured to create a substantial pressure drop between main channel 430 and well 172 when negative or positive pressure is applied to wells 172 via the manifold.

The main channel also may communicate with a sensor port 440 and a pressure port 442 via channels 434, 436. The sensor port may be engaged with coupling 414 (see FIG. 19) to enable fluid communication between the main channel and pressure sensor 90. The pressure port may be engaged with coupling 416 (see FIG. 19), to enable application of negative and/or positive pressure to chip 152 via ports 76. The main channel may be sealed at its opposing ends by plugs 444.

In some embodiments, the manifold may permit emulsion formation to be started and stopped independently for each emulsion. The manifold may have a valve at each port so that each port corresponding to a different droplet generator can be individually controlled. In other words, each droplet generator can have pressure applied individually instead of or in addition to all ports/droplet generators at once. Each port/droplet generator may have its own sensor to detect a change (pressure, optical, etc.) indicating an endpoint of droplet generation. Thus, each droplet generator may be actuated independently and sensed independently.

VII. Exemplary Structure and Operation of a Drive Assembly for the Instrument This section describes exemplary structure and operation of drive assembly 60 of instrument 52; see FIGS. 21 and 22.

FIG. 21 shows manifold 72 and door 126 (in phantom outline) in a retracted configuration (e.g., see FIG. 2) in which instrument 52 is open for loading and unloading cassette 54. The manifold may be elevated with respect to its prospective engaged position with gasket 154.

FIG. 22 shows manifold 72 and door 126 in an extended configuration in which instrument 52 is closed (cassette 54 is not accessible to the user) and manifold 72 is in a lowered position, in engagement with gasket 154.

Operation of drive assembly 60 may drive movement of manifold 72 and door 126 between the configurations shown in FIGS. 21 and 22. Both manifold 72 and door 126 may be supported by carriage 104. Accordingly, travel of carriage 104 horizontally on a linear path along track 396, may move both the manifold and the door forward and backward in the instrument. Movement of carriage 104 may be driven by motor 100 (e.g., see FIG. 18). Carriage 104 and motor 100 may be linked by rack-and-pinion linkage 108, which may be formed by a rack 460 that engages a gear (a pinion) 462. Rack 460 may be mounted to carriage 104, and gear 462 may be turned by operation of motor 100. After the manifold has been driven to a position above gasket 154, motor 102 may be operated to turn lead screw 404 of linkage 109, to lower manifold 72 into engagement with gasket 154.

VIII. Selected Embodiments

This section describes selected embodiments of the present disclosure as a series of indexed paragraphs. These embodiments should not limit the entire scope of the present disclosure.

A. A method of emulsion formation, comprising: (i) applying pressure to a microfluidic chip holding prospective emulsion phases, to drive droplet formation and collection of emulsions in the chip; (ii) monitoring the pressure for a change that meets a predefined condition; and (iii) stopping application of the pressure when the change is detected.

B. The method of paragraph A, wherein the chip includes output containers that collect the emulsions and input containers that hold the prospective emulsion phases, and wherein the pressure includes positive pressure applied to at least a subset of the input containers, negative pressure applied to the output containers, or both positive pressure applied to at least a subset of the input containers and negative pressure applied to the output containers.

C. The method of paragraph A or B, wherein the chip provides input wells for holding the prospective emulsion phases and output wells for collecting the emulsions.

D. The method of any of paragraphs A to C, wherein the pressure is applied with a gas phase that contacts liquid contained completely by the chip.

E. The method of any of paragraphs A to D, wherein the gas phase is composed of air.

F. The method of any of paragraphs A to E, wherein the pressure is a first pressure applied with an instrument having a pressure sensor, and wherein the pressure sensor monitors the first pressure by detecting a second pressure corresponding to the first pressure.

G. The method of claim F, wherein the instrument includes a fluidics assembly with a manifold providing a plurality of ports through which the first pressure is applied to the chip, wherein the second pressure is detected in a region of the fluidics assembly that is fluidically connected to the ports, and wherein the ports provide a resistance to fluid flow that reduces a magnitude of the first pressure relative to the second pressure.

H. The method of paragraph G, wherein the manifold includes a main channel and a plurality of side channels that branch from the main channel, wherein the side channels form the ports, and wherein the second pressure corresponds more closely to pressure in the main channel than the side channels.

I. The method of any of paragraphs A to H, wherein air following liquid into one or more channels of the chip leads to the change in the pressure.

J. The method of paragraph I, wherein the prospective emulsion phases are held by a plurality of input wells of the chip, and wherein the change in the pressure occurs if only one of the input wells is empty.

K. The method of any of paragraphs A to J, wherein the prospective emulsion phases are held by input containers, wherein application of the pressure drives the phases through channels of the chip for droplet formation and collection as emulsions in output containers of the chip, and wherein application of the pressure is stopped after air has followed liquid into one or more of the channels from one or more of the input containers and before the air has reached all of the emulsions collected in the output containers.

L. The method of any of paragraphs A to K, wherein the prospective emulsion phases include a plurality of samples, and wherein application of the pressure is stopped when at least about 80% by volume of each of the samples has been converted to droplets.

M. The method of any of paragraphs A to L, wherein the pressure is applied with a fluidics assembly engaged with a gasket defining a plurality of orifices, and wherein the orifices provide fluid communication between the chip and the fluidics assembly.

N. The method of paragraph M, further comprising a step of connecting the gasket to the chip before application of the pressure.

O. The method of paragraph M, wherein the chip includes a plurality of input wells and a plurality of output wells, and wherein the gasket is connected to the chip such that each of the input wells and/or each of the output wells is at least partially covered by the gasket.

P. The method of paragraph O, wherein each of the input wells and each of the output wells is only partially covered by the gasket.

Q. The method of any of paragraphs A to P, wherein the pressure is applied by an instrument, further comprising a step of attaching the chip to a cartridge and a step of disposing the chip attached the cartridge in a receiving area of the instrument before the pressure is applied.

R. The method of paragraph Q, further comprising a step of attaching a gasket to the cartridge such that orifices of the gasket overlap wells of the chip.

S. The method of any of paragraphs A to R, wherein the pressure originates from a pump, and wherein the pressure is applied while the pump is fluidically isolated from the chip, not pumping fluid, or both fluidically isolated from the chip and not pumping fluid.

T. The method of any of paragraphs A to S, further comprising a step of establishing negative or positive gas pressure in a reservoir, wherein the step of applying pressure includes (1) a step of creating fluid communication between the reservoir and the chip and (2) a step of maintaining the fluid communication while the established pressure drives droplet formation and collection of emulsions in the chip without modification of the established pressure by a pump.

U. The method of paragraph T, wherein the reservoir is a conduit.

V. The method of paragraph U, wherein the conduit fluidically connects a pressure controller to a valve.

W. The method of any of paragraphs A to V, further comprising: (1) disposing the chip in a receiving area of an instrument; (2) dispensing the prospective emulsions phases into wells of the chip; and (3) inputting an actuation signal to the instrument, wherein the actuation signal causes the instrument to apply the pressure to the chip to drive formation and collection of emulsions in parallel in the chip, and to stop application of the pressure when an endpoint of emulsion formation has been reached.

X. The method of any of paragraphs A to W, wherein the emulsions are collected in output containers of the chip, further comprising a step of concentrating the emulsions by selectively driving a continuous phase of an emulsion from each of the output containers.

Y. The method of paragraph X, wherein the pressure is a negative pressure, and wherein the step of concentrating is performed by application of positive pressure to the chip.

Z. The method of paragraph X, wherein the step of applying pressure is performed for a first length of time, and wherein the step of concentrating is performed by applying pressure for a second length of time that is based on the first length of time.

A1. The method of paragraph Z, wherein the second length of time is proportional to the first length of time.

B1. The method of any of paragraphs A to Z and A1, wherein the chip is a first microfluidic chip, further comprising: (i) disposing the first microfluidic chip and a first gasket defining a plurality of orifices in a receiving area of an instrument, with the first gasket connected to the first chip; (ii) removing the first chip and the first gasket from the receiving area after the step of stopping application of the first pressure; and (iii) repeating the steps of disposing, applying, stopping, and removing with a second microfluidic chip and a second gasket.

C1. The method of paragraph B1, wherein the first chip and the first gasket are disposable and are thrown away after removal from the receiving area of the instrument.

D1. A method of emulsion formation, comprising: (i) applying pressure to a microfluidic chip holding prospective emulsion phases in input containers, to drive the phases through channels of the chip for droplet formation and collection as emulsions in output containers of the chip; and (ii) stopping application of the pressure after air has followed liquid into one or more of the channels from one or more of the input containers and before the air has reached all of the emulsions collected in the output containers.

E1. The method of paragraph D1, wherein the pressure is at least one first pressure applied with an instrument including a fluidics assembly having a pressure sensor, wherein the pressure sensor detects a second pressure in the fluidics assembly, and wherein the instrument stops application of the first pressure when the second pressure exhibits a change that meets a predefined condition.

F1. A system for emulsion formation, comprising: (i) a microfluidic chip configured to hold prospective emulsion phases; and (ii) an instrument including a fluidics assembly having a pressure sensor, the instrument being configured to apply pressure to the chip with the fluidics assembly to drive droplet generation and collection of emulsions in the chip, to monitor the pressure with a pressure sensor for a change indicating an endpoint of droplet generation has been reached, and to stop application of the pressure when the change is detected by the pressure sensor.

G1. The system of paragraph F1, further comprising a gasket defining a plurality of orifices configured to provide fluid communication between the chip and the fluidics assembly such that the pressure can be applied by the fluidics assembly.

H1. The system of paragraph G1, wherein the chip has a plurality of wells, and wherein the gasket is configured to be engaged with the chip such that a different orifice of the gasket overlaps each well.

I1. The system of any of paragraphs F1 to H1, wherein the chip includes input wells interconnected with output wells by channels, wherein the instrument is configured to stop application of the pressure after air has followed liquid into one or more of channels from one or more of the input wells and before the air has reached all of the emulsions collected in the output wells.

J1. The system of any of paragraphs F1 to I1, wherein the instrument is configured to receive an actuation signal from a user after the chip holding the emulsion phases is received by the instrument, and wherein the actuation signal causes the instrument, without any further user input or participation, to apply the pressure, to monitor the pressure, and to stop application of the pressure.

K1. The system of any of paragraphs F1 to J1, wherein the fluidics assembly includes a pump that functions as a source of the pressure, and wherein the pressure is applied by the instrument while the pump is fluidically isolated from the chip, not pumping fluid, or both fluidically isolated from the chip and not pumping fluid.

L1. A method of emulsion formation, comprising: (i) applying pressure to a microfluidic chip holding samples and at least one continuous phase, to drive formation of droplets and collection of emulsions in the chip; and (ii) stopping application of the pressure when at least 80% by volume of each of the samples has been converted to droplets.

M1. A method of emulsion formation, comprising: (i) dispensing prospective emulsions phases into wells of a microfluidic chip; (ii) disposing the chip in a receiving area of an instrument; and (iii) inputting an actuation signal to the instrument, wherein the actuation signal causes the instrument to apply pressure to the chip to drive formation and collection of emulsions in parallel in the chip, and to stop application of pressure when an endpoint of emulsion formation has been reached.

N1. The method of paragraph M1, further comprising a step of connecting the chip to a gasket before the step of disposing.

O1. The method of paragraph M1 or N1, wherein the chip includes a plurality of wells, and wherein the gasket is connected to the chip such that wells of the chip are at least partially covered by the gasket.

P1. The method of paragraph N1, further comprising a step of connecting the chip to a cartridge before the step of disposing, wherein the cartridge acts a holder for the chip.

Q1. The method of paragraph P1, wherein the cartridge engages the gasket to attach the gasket to the cartridge.

R1. A method of emulsion formation, comprising: (i) applying pressure to a microfluidic chip holding prospective emulsion phases, to drive droplet formation and collection of emulsions in the chip; (ii) monitoring with at least one sensor an aspect of liquid held by the chip and/or of a fluid volume in contact with the liquid for a change that indicates an endpoint for droplet generation has been reached; and (iii) stopping application of the pressure when the change is detected.

S1. The method of paragraph R1, wherein the prospective emulsion phases includes samples and volumes of one or more continuous phases, wherein the step of stopping is based on one or more signals from a sensor that monitors an aspect of one or more of the samples, one or more of the volumes, fluid in contact with liquid held by the chip, or a combination thereof.

T1. The method of paragraph R1 or S1, wherein the chip is included in a cassette having a gasket disposed over the chip, wherein pressure application is performed with an instrument, further comprising a step of removing the cassette as a unit from the instrument after application of pressure is stopped.

U1. A method of forming an emulsion, comprising: (i) driving a first phase and an immiscible second phase through a droplet generator and forward along a flow path connecting the droplet generator to a container, such that an emulsion of first phase droplets disposed in the second phase is collected in the container; and (ii) decreasing a volume fraction of the second phase in the collected emulsion by selectively driving the second phase from the container in reverse along the flow path.

V1. The method of paragraph U1, wherein the droplet generator is formed by an intersection of at least one inlet channel for each respective phase and an outlet channel to carry the emulsion, and wherein the outlet channel extends from the droplet generator to a bottom region of the container.

W1. The method of paragraph U1 or V1, wherein the first phase is an aqueous phase including nucleic acid, wherein the second phase is an oil phase, and wherein the emulsion has an average of about two genome-equivalents or less of the nucleic acid per droplet.

X1. The method of any of paragraphs U1 to W1, wherein the step of driving includes a step of applying a negative gas pressure to the container to draw the first and second phases to the container.

Y1. The method of any of paragraphs U1 to X1, wherein the step of decreasing a volume fraction of the second phase includes a step of applying a positive gas pressure to the container to push the second phase from the container.

Z1. The method of any of paragraphs U1 to Y1, wherein the droplets of the first phase are buoyant in the second phase, further comprising a step of permitting a substantially droplet-free volume of the second phase to form in the collected emulsion under the droplets after the step of driving and before the step of decreasing the volume fraction.

A2. The method of any of paragraphs U1 to Z1, wherein the step of driving is performed for a first length of time, and wherein the step of decreasing a volume fraction is performed for a second length of time that is based on the first length of time.

B2. The method of paragraph A2, wherein the second length of time is proportional to the first length of time.

C2. The method of any of paragraphs U1 to Z1, A2, and B2, further comprising a step of loading the first phase into a first reservoir and the second phase into a second reservoir, wherein the step of driving urges the first phase and the second phase to the droplet generator from the first reservoir and the second reservoir, respectively, and wherein the step of decreasing the volume fraction includes a step of driving at least a portion of the second phase into the first reservoir, the second reservoir, or both the first reservoir and the second reservoir.

D2. The method of paragraph C2, wherein the container and each reservoir is a well.

E2. The method of any of paragraphs U1 to Z1 and A2 to D2, wherein the step of driving is performed in parallel with a microfluidic chip including a plurality of droplet generators and a plurality of containers that collect emulsions created by respective droplet generators, and wherein the step of decreasing a volume fraction is performed in parallel on each of the collected emulsions.

F2. The method of paragraph E2, wherein the step of driving and the step of decreasing a volume fraction are each performed with pressure transmitted to the chip by a same manifold.

G2. A system for emulsion formation, comprising: (i) an instrument including a fluidics assembly having a pressure source; and (ii) a microfluidic chip including a droplet generator, a container, and respective reservoirs configured to hold a first phase and an immiscible second phase, wherein the instrument is configured to receive the chip and to apply pressure from the fluidics assembly to the chip to drive the first and second phases through the droplet generator and to the container such that an emulsion of first phase droplets disposed in the second phase is formed by the droplet generator and collected in the container, and also is configured to decrease a volume fraction of the second phase in the collected emulsion by selectively driving the second phase from the container and into at least one of the reservoirs.

H2. The system of paragraph G2, wherein the pressure source includes a vacuum pump, and wherein the pressure applied to the chip is a negative pressure applied to the container such that the first phase and a second phase are drawn from the reservoirs to the container.

I2. The system of paragraph G2 or H2, wherein the pressure source includes a first pump and a second pump, wherein the first pump generates negative pressure and the second pump generates positive pressure, and wherein the negative pressure and the positive pressure are applied serially to the chip, with the positive pressure being applied before or after the negative pressure.

J2. The system of paragraph I2, wherein negative pressure generated by the first pump causes the emulsion to be formed and collected, and wherein positive pressure generated by the second pump causes the volume fraction of the second phase to be decreased.

K2. The system of any of paragraphs G2 to J2, wherein a first pressure is applied to the chip for a first length of time to form and collect the emulsion, wherein a second pressure is applied to the chip for a second length of time to decrease a volume fraction of the second phase in the collected emulsion, and wherein the instrument is configured to determine the second length of time based on the first length of time.

L2. The system of any of paragraphs G2 to K2, further comprising a gasket disposed over the chip, wherein the chip includes a plurality of droplet generators and containers to receive emulsions from respective droplet generators, and wherein the fluidics assembly includes a manifold that operatively engages the gasket to create fluid communication between the fluidics assembly and the chip.

M2. The system of paragraph L2, wherein the manifold has a plurality of ports, and wherein each port provides fluid communication with a different one of the containers when the manifold is engaged with the gasket.

N2. A method of emulsion formation, comprising: (i) establishing negative or positive gas pressure in a reservoir; (ii) creating fluid communication between the reservoir and a microfluidic chip holding prospective emulsion phases; and (ii) maintaining the fluid communication while the established pressure drives droplet formation and collection of emulsions in the chip without modification of the established pressure by a pump.

O2. The method of paragraph N2, wherein the reservoir is a conduit.

P2. The method of paragraph O2, wherein the conduit connects a pressure controller to a valve.

Q2. The method of any of paragraphs N2 to P2, wherein the reservoir includes a first reservoir fluidically disposed between a pressure controller and a manifold and a second reservoir fluidically disposed between a pump and the pressure controller, and wherein the step of maintaining includes a step of adjusting fluid communication between the first and second reservoirs with the pressure controller.

R2. A method of emulsion formation, comprising: (i) disposing a first microfluidic chip and a first gasket defining a plurality of orifices in a receiving area of an instrument, with the first gasket connected to the first chip; (ii) applying pressure with an instrument to the first microfluidic chip via the orifices to drive droplet formation and collection of emulsions in the first chip; (iii) removing the first chip and the first gasket from the receiving area; and (iv) repeating the steps of disposing, applying, and removing with a second microfluidic chip and a second gasket.

S2. The method of paragraph R2, wherein the first chip and the first gasket are connected to each other before they are disposed in the receiving area.

T2. The method of paragraph R2 or S2, further comprising a step of discarding the first chip and the first gasket after the step of removing, or a step of discarding the first chip and reusing the first gasket as the second gasket.

U2. The method of any of paragraphs R2 to T2, wherein the first chip has a plurality of wells, and wherein the first gasket connected to the first chip only partially covers each of the wells.

V2. The method of paragraph U2, wherein each well of the first chip is overlapped by an orifice of the first gasket.

W2. The method of any of paragraphs R2 to V2, wherein the first chip has a plurality of input wells and a plurality of output wells, and wherein each input well and/or each output well is larger in diameter than an orifice of the first gasket that overlaps such well.

X2. The method of paragraph W2, wherein each input well and/or each output well has a rim, and wherein the first gasket is configured to form a seal circumferentially with the rim of each input well and/or each output well.

Y2. The method of any of paragraphs R2 to X2, further comprising a step of attaching the first chip to a cartridge that holds the first chip and connects the first gasket to the first chip.

Z2. A device for forming emulsions, comprising: (i) a microfluidic chip including a plurality of droplet generators, a plurality of input wells configured to hold and supply prospective emulsion phases for the droplet generators, and a plurality of output wells configured to receive and collect emulsions produced by the droplet generators from the emulsion phases; and (ii) a gasket defining a plurality of orifices and configured to be disposed on and engaged with the chip such that each of the input wells and/or each of the output wells is only partially covered by the gasket.

A3. A device for forming emulsions, comprising: (i) a microfluidic chip including a plurality of droplet generators, a plurality of input wells configured to hold and supply prospective emulsion phases for the droplet generators, and a plurality of output wells configured to receive and collect emulsions produced by the droplet generators from the emulsion phases; and (ii) a gasket defining an array of orifices and configured to be disposed on and engaged with the chip such that each well is overlapped by a different orifice.

B3. The device of paragraph A3, wherein each well is larger in diameter than the orifice that overlaps such well.

C3. The device of paragraph A3 or B3, wherein each output well has a rim, and wherein the gasket is configured to form a seal circumferentially with the rim.

D3. A device for forming emulsions, comprising: (i) a microfluidic chip including a plurality of droplet generators, a plurality of input wells configured to hold and supply prospective emulsion phases for the droplet generators, and a plurality of output wells configured to receive and collect emulsions produced by the droplet generators from the emulsion phases; and (ii) a gasket defining an array of orifices and configured to be disposed on and engaged with the chip such that each output well, each input well, or each output well and each input well is overlapped by a different orifice.

E3. The device of paragraph D3, wherein the gasket is configured to cover only a portion of each well that is overlapped.

F3. The device of paragraph D3 or E3, wherein the gasket is configured to cover only a perimeter portion of each well that is overlapped.

G3. The device of any of paragraphs D3 to F3, wherein each well that is overlapped is larger in diameter than the orifice that overlaps such well.

H3. The device of any of paragraphs D3 to G3, wherein each well overlapped by an orifice has a rim, and wherein the gasket is configured to form a seal circumferentially with the rim.

I3. The device of any of paragraphs D3 to H3, further comprising a cartridge that receives and holds the chip.

J3. The device of paragraph I3, wherein the cartridge includes a plurality of projections, and wherein the gasket defines apertures configured to be received on the projections to attach the gasket to the cartridge with the orifices overlapping the wells.

K3. The device of paragraph I3, wherein the cartridge has a locked configuration and an unlocked configuration that respectively restrict and permit removal of the chip from the cartridge.

L3. The device of paragraph I3, wherein the cartridge includes an electrically conductive contact element.

M3. The device of paragraph L3, wherein the contact element is disposed on a bottom surface of the cartridge.

N3. The device of any of paragraphs I3 to M3, wherein an upper surface region of the cartridge includes an optical element configured to reflect light, and wherein the gasket attached to the cartridge blocks light reflection by the optical element.

O3. The device of any of paragraphs I3 to N3, wherein the cartridge has a substantially larger footprint than the chip, optionally having a footprint area that is at least twice that of the chip.

P3. A method of forming emulsions, comprising: (i) selecting a gasket defining a plurality of orifices and a microfluidic chip including a plurality of droplet generators, a plurality of input wells configured to hold and supply prospective emulsion phases to the droplet generators, and a plurality of output wells; (ii) disposing the gasket in engagement with the chip such that each output well, each input well, or each output well and each input well is overlapped by an orifice of the gasket; and (iii) engaging the gasket with a port interface of a fluidics assembly including a pump, to apply pressure to the input wells, the output wells, or both to drive the emulsion phases from the input wells, through the droplet generators, and to the output wells for collection as emulsions.

Q3. The method of paragraph P3, wherein the port interface is a manifold. R3. The method of paragraph P3 or Q3, wherein each overlapped well is overlapped by a different orifice.

S3. A method of emulsion formation, comprising: (i) applying pressure with gas to drive a first phase and an immiscible second phase through a droplet generator and along a flow path connecting the droplet generator to a container, such that an emulsion of first phase droplets disposed in the second phase is formed by the droplet generator and collected in the container; (ii) monitoring the pressure for a change that meets a predefined condition; and (iii) terminating application of the pressure if the change occurs.

T3. The method of paragraph S3, wherein the step of applying pressure includes a step of applying negative pressure to the container such that the first phase and the second phase are drawn to the container by the negative pressure.

U3. The method of paragraph S3 or T3, wherein the step of applying pressure drives parallel droplet formation at respective droplet generators and parallel collection of a plurality of emulsions in separate containers.

V3. The method of paragraph U3, wherein the step of applying pressure is performed with a manifold disposed in fluid communication with each of the separate containers.

W3. The method of paragraph V3, wherein the change in pressure is indicative of air traveling through a droplet generator and along a flow path to a container.

X3. The method of any of paragraphs S3 to W3, wherein the pressure is a negative pressure, and wherein the change includes a decrease in the magnitude of the negative pressure.

Y3. The method of any of paragraphs S3 to X3, wherein the droplet generator is supplied with the first phase and the second phase from respective reservoirs, and wherein at least one of the respective reservoirs being empty can produce the change.

Z3. The method of any of paragraphs S3 to Y3, wherein the step of applying pressure drives parallel droplet formation at respective droplet generators and parallel collection of a plurality of emulsions in separate containers, wherein the droplet generators are supplied with first and second phases from a plurality of reservoirs, and wherein the change in pressure is indicative of any one of the reservoirs being empty.

A4. The method of any of paragraphs S3 to Z3, wherein the first phase is an aqueous phase containing a nucleic acid target, and wherein the target is present at an average concentration of no more than about two copies per droplet in the emulsion.

B4. The method of any of paragraphs S3 to Z3 and A4, wherein the first phase is an aqueous phase containing genomic DNA, and wherein the genomic DNA is present at an average concentration of no more than about two genome-equivalents per droplet in the emulsion.

C4. A system for emulsion formation, comprising: (i) an instrument including a fluidics assembly having a pressure source and a pressure sensor that monitors pressure in the fluidics assembly; and (ii) a cassette including a chip providing a droplet generator, a container, and respective reservoirs configured to hold a first phase and an immiscible second phase, wherein the instrument is configured to receive the cassette and to apply a pressure with gas to the chip to drive the first and second phases through the droplet generator and to the container such that an emulsion of first phase droplets disposed in the second phase is formed by the droplet generator and collected in the container, and also is configured to monitor the pressure for a change that meets a predefined condition indicating depletion of liquid from a reservoir, and to terminate application of the pressure if the change occurs.

D4. An apparatus for driving emulsification of prospective emulsion phases held by a cassette including a plurality of droplets generators, input reservoirs to hold the emulsion phases for the droplet generators, and containers to collect emulsions, the apparatus comprising: (i) a seating area for the cassette; (ii) a fluidics assembly including one or more ports; (iii) a drive assembly operative to provide relative movement of the ports and the cassette disposed in the seating area; (iv) a user control; and (v) a processor, wherein a single actuation signal communicated to the processor from the user control causes (1) the drive assembly to create fluid communication between the ports and the cassette, and (2) the fluidics assembly to drive, via gas pressure at the ports, the prospective emulsion phases through the droplet generators and to the containers for collection as emulsions.

E4. The apparatus of paragraph D4, wherein the fluidics assembly includes a vacuum pump, and wherein the fluidics assembly drives the prospective emulsion phases to the droplet generators by application of negative gas pressure to the cassette via the ports.

F4. The apparatus of paragraph D4 or E4, wherein the fluidics assembly has a different port for each droplet generator.

G4. The apparatus of paragraph F4, wherein the fluidics assembly includes a manifold that provides the ports, and wherein the single actuation signal causes the drive assembly to move the manifold into engagement with the cassette.

H4. The apparatus of paragraph G4, wherein the cassette includes a chip and a gasket, wherein the chip provides the droplet generators, the reservoirs, and the containers, and wherein the gasket forms a seal at a perimeter of each of the containers, each of the reservoirs, or each of the containers and each of the reservoirs.

I4. The apparatus of paragraph H4, wherein the gasket forms a seal at a perimeter of each of the containers and with each of the reservoirs.

J4. The apparatus of paragraph H4, wherein the gasket is perforated to provide a respective orifice that vent each of the containers, each of the reservoirs, or each of the containers and each of the reservoirs.

K4. The apparatus of paragraph J4, wherein each orifice has a smaller diameter than the container or reservoir that the orifice vents, such that the gasket covers a majority of each container, reservoir, or container and reservoir.

L4. The apparatus of any of paragraphs D4 to K4, further comprising a door, wherein the seating area is disposed in a chamber that is formed in part by the door, and wherein the single actuation signal causes the door to close such that the seating area is not accessible to a user.

M4. The apparatus of any of paragraphs D4 to L4, wherein the emulsion phases are driven by application of positive or negative gas pressure at the ports, wherein the single actuation signal also causes the fluidics assembly to terminate application of the gas pressure at the ports if a predefined condition representing an endpoint for emulsion formation is detected.

N4. The apparatus of any of paragraphs D4 to M4, wherein the single actuation signal is provided by a switch.

O4. The apparatus of paragraph N4, wherein the switch is operated by pushing a button.

P4. The apparatus of any of paragraphs D4 to O4, further comprising a sensor configured to detect whether or not at least part of the cassette is disposed in the seating area, and wherein the instrument does not implement the actuation signal if the sensor detects that the cassette is not disposed in the seating area.

Q4. The apparatus of any of paragraphs D4 to P4, wherein the cassette includes a microfluidic chip and a gasket disposed on the chip, further comprising a sensor configured to detect whether or not the gasket is present in the seating area, wherein the instrument does not implement the actuation signal if the sensor detects that the gasket is not present.

R4. A system for emulsion formation, comprising: (i) an instrument including a fluidics assembly capable of generating pressure; and (ii) a cassette including a cartridge and a microfluidic chip configured to be received and held by the cartridge, the chip including a plurality of droplet generators, a plurality of reservoirs configured to hold and supply prospective emulsion phases for the droplet generators, and a plurality of containers, wherein the instrument is configured to receive the cassette and to apply pressure to the chip with the fluidics assembly to drive the phases through the droplet generators and to the containers for collection as emulsions.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

The invention claimed is:

1. A method of generating droplets, the method comprising:
   selecting a device including a plurality of emulsion-formation units each including a sample well, a continuous-phase well, a droplet well, and a channel network that fluidically interconnects the wells and creates a droplet-generation region;
   placing a discrete volume of sample-containing fluid into the sample well of each emulsion-formation unit, and a discrete volume of continuous-phase fluid into the continuous-phase well of each emulsion-formation unit;
   applying pressure to the device with a fluidics assembly after the step of placing, such that in each emulsion-formation unit (a) sample-containing fluid flows from the sample well to the droplet-generation region, (b) continuous-phase fluid flows from the continuous-phase well to the droplet-generation region, and (c) sample-containing droplets and continuous-phase fluid flow from the droplet-generation region to the droplet well, wherein the plurality of emulsion-formation units generate droplets in parallel with one another;
   detecting a pressure signal from the fluidics assembly; and
   stopping application of the pressure when the pressure signal indicates that a sample well is empty.

2. The method of claim 1, wherein the device has a row of sample wells, a row of continuous-phase wells, and a row of droplet wells, and wherein the step of applying pressure includes a step of applying pressure in parallel to each well of at least one of the rows of wells, and wherein the step of stopping application of the pressure includes a step of stopping application of pressure in parallel to each well of the at least one row of wells.

3. The method of claim 1, wherein the step of stopping application of the pressure includes a step of adjusting a valve to vent a portion of the fluidics assembly that is applying the pressure.

4. The method of claim 1, wherein the step of applying pressure includes a step of applying negative pressure in parallel to each of the droplet wells, and wherein the step of stopping application of the pressure includes a step stopping application of the negative pressure to each of the droplet wells.

5. The method of claim 4, wherein the fluidics assembly includes a manifold, wherein the negative pressure is applied via the manifold, and wherein the manifold is sealed to each of the droplet wells via a same gasket.

6. The method of claim 1, wherein the fluidics assembly includes a pressure reservoir that is operatively connected to a pump, wherein the pump is configured to create negative or positive pressure in the pressure reservoir, and wherein the step of applying pressure includes a step of applying negative or positive pressure via the pressure reservoir while the pressure reservoir remains isolated from the pump.

7. The method of claim 1, the pressure being first pressure, further comprising a step of applying second pressure after the step of stopping application, such that continuous-phase fluid is removed selectively, relative to droplets, from an emulsion present in each droplet well.

8. The method of claim 7, wherein the second pressure includes positive pressure applied to each of the droplet wells.

9. The method of claim 7, wherein the second pressure causes continuous-phase fluid to flow from the droplet well of each emulsion-formation unit via a channel that connects the droplet well to the corresponding droplet-generation region.

10. The method of claim 7, wherein the step of applying first pressure is performed for a first length of time, and wherein the step of applying second pressure is performed for a second length of time that is based on the first length of time.

11. A method of generating droplets, the method comprising:
    selecting a device including a plurality of separate emulsion-formation units each including a sample well, a continuous-phase well, a droplet well, and a channel network that fluidically interconnects the wells and creates a droplet-generation region;
    placing a discrete volume of sample-containing fluid into the sample well of each emulsion-formation unit, and a discrete volume of continuous-phase fluid into the continuous-phase well of each emulsion-formation unit;

applying negative pressure to the droplet well of each of the emulsion-formation units via a manifold after the step of placing, with the manifold sealed to each droplet well via a same gasket, such that in each emulsion-formation unit (a) sample-containing fluid flows from the sample well to the droplet-generation region, (b) continuous-phase fluid flows from the continuous-phase well to the droplet-generation region, and (c) sample-containing droplets and continuous-phase fluid flow from the droplet-generation region to the droplet well, wherein the plurality of emulsion-formation units generate droplets in parallel with one another;

detecting a pressure signal corresponding to the negative pressure; and stopping application of negative pressure to all of the droplet wells in parallel when the pressure signal indicates that air has entered the channel network of an emulsion-formation unit.

12. The method of claim 11, wherein the step of stopping application includes a step of adjusting a valve to vent each droplet well.

13. The method of claim 11, wherein the manifold is connected to a pressure reservoir that is operatively connected to a pump, wherein the pump is configured to create negative pressure in the pressure reservoir, and wherein the step of applying negative pressure is performed via the pressure reservoir while the pressure reservoir remains isolated from the pump.

14. The method of claim 11, further comprising a step of applying positive pressure in parallel to each of the droplet wells after the step of stopping application, such that continuous-phase fluid is removed selectively, relative to droplets, from an emulsion present in each droplet well.

15. The method of claim 14, wherein the positive pressure causes continuous-phase fluid to flow from the droplet well of each emulsion-formation unit via a channel that connects the droplet well to the corresponding droplet-generation region.

16. The method of claim 14, wherein the step of applying negative pressure is performed for a first length of time, and wherein the step of applying positive pressure is performed for a second length of time that is based on the first length of time.

* * * * *